US012714672B2

(12) United States Patent
Chang et al.

(10) Patent No.: US 12,714,672 B2
(45) Date of Patent: Aug. 25, 2026

(54) AQUATIC LIPOSOMES ENCAPSULATING NATURAL COMPOUNDS AND MANUFACTURING METHOD THEREOF

(71) Applicant: Chung Shan Medical University, Taichung City (TW)

(72) Inventors: Yuan-Yen Chang, Taichung City (TW); Hui-Wen Lin, Taichung City (TW); Yi-Feng Kao, Keelung City (TW)

(73) Assignee: CHUNG SHAN MEDICAL UNIVERSITY, Taichung City (TW)

( * ) Notice: Subject to any disclaimer, the term of this patent is extended or adjusted under 35 U.S.C. 154(b) by 222 days.

(21) Appl. No.: 18/600,544

(22) Filed: Mar. 8, 2024

(65) Prior Publication Data

US 2024/0342089 A1 Oct. 17, 2024

(30) Foreign Application Priority Data

Mar. 9, 2023 (TW) ................................ 112108673

(51) Int. Cl.

*A61K 9/1277* (2025.01)
*A61K 31/12* (2006.01)
*A61K 31/352* (2006.01)

(52) U.S. Cl.

CPC ............ *A61K 9/1277* (2013.01); *A61K 31/12* (2013.01); *A61K 31/352* (2013.01)

(58) Field of Classification Search

CPC ..... A61K 9/1277; A61K 31/12; A61K 31/352
See application file for complete search history.

(56) References Cited

U.S. PATENT DOCUMENTS 4,544,545 A * 10/1985 Ryan .................... A61K 9/1271 424/9.4
2019/0201463 A1* 7/2019 Kariman ............ A61K 36/3482
2022/0265555 A1* 8/2022 Klein ...................... A61K 9/127
2024/0122853 A1* 4/2024 Moon ................ A61K 41/0028

OTHER PUBLICATIONS

Kohn (https://tovatech.com/blog/1504/ultrasonic-cleaner-blogs/sonicator-baths-sample-prep-pharma-research#:~:text=What%20is%20a%20Laboratory%20Sonicator?%20A%20laboratory,hearing%20range%E2%80%94to%20create%20high%2Dfrequency%20energy%20in%20liquids) Mar. 20, 2025, pp. 1-7 (Year: 2025).*

* cited by examiner

*Primary Examiner* — Andrew S Rosenthal
(74) *Attorney, Agent, or Firm* — Birch, Stewart, Kolasch & Birch, LLP

(57) ABSTRACT

An aquatic liposome encapsulating a natural compound is provided, wherein an average particle size (a median particle size) of the aquatic liposome encapsulating the natural compound ranges from 80 nm to 200 nm. A manufacturing method of an aquatic liposome encapsulating a natural compound is provided and includes performing an ultrasonic oscillation after mixing the aquatic liposome and the natural compound, so that the natural compound is encapsulated in the aquatic liposome. Experiments are conducted to prove that the aquatic liposome encapsulating the natural compound could effectively enter microglia and retinal pigment epithelium cells to relieve the inflammatory response and hinder the apoptosis.

16 Claims, 21 Drawing Sheets
(2 of 21 Drawing Sheet(s) Filed in Color)

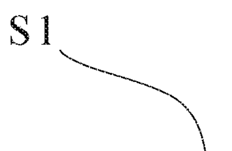

Provide aquatic liposome and mix aquatic liposome with natural compound, wherein mixed concentration of aquatic liposome ranges from 0.05mg/ml to 1.0mg/ml

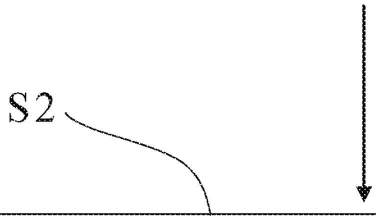

Perform ultrasonic oscillation after mixing aquatic liposome and natural compound, so that natural compound is encapsulated in aquatic liposome

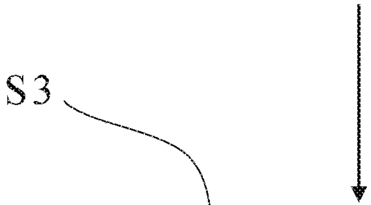

Measure aquatic liposome, wherein average particle size ( median particle size) of aquatic liposome encapsulating natural compound ranges from 80nm to 200nm

FIG.1

Mock Control group Experimental group

AQUATIC LIPOSOMES ENCAPSULATING NATURAL COMPOUNDS AND MANUFACTURING METHOD THEREOF

BACKGROUND OF THE INVENTION

Technical Field

The present invention relates generally to a technology of using liposomes, and more particularly to an aquatic liposome encapsulating a natural compound and a manufacturing method thereof.

Description of Related Art

In general, a "liposome" is mainly applied as a carrier for a medication or a nutrient and are mainly adapted to encapsulate the medication or the nutrient and transport the medication or the nutrient to a target organ. The structure of the liposome could prevent the liposome from being removed by phagocytosis of macrophages during absorption and could slowly release the medication or the nutrient encapsulated.

Conventional research on the preparation of liposomes shows that aquatic products are rarely used as extraction sources. The process of the aquatic products emerges aquatic waste, such as fish skin and fish head. The phospholipids extracted from such aquatic waste typically contain a large amount of DHA, EPA, DPA, and ARA, which could relieve the cellular inflammation of the animal. However, there are currently no relevant studies exploring the use of aquatic product extraction to prepare liposomes to coat specific drugs to the anti-inflammatory effect.

Tetrahydrocurcumin (THC) is a metabolite of curcumin (CUR). In addition to having higher water solubility, chemical stability, and bioavailability compared to CUR, it also possesses many of the beneficial biological activities of CUR. Therefore, how to extract and prepare a liposome from an aquatic product for encapsulating tetrahydrocurcumin (THC), is a problem to be solved of the present invention.

BRIEF SUMMARY OF THE INVENTION

Given the above, the primary objective of the present invention is to provide an aquatic liposome encapsulating a natural compound and a manufacturing method thereof, wherein the aquatic liposome encapsulates the natural compound into specific particle sizes that could efficiently enter cells.

The present invention provides an aquatic liposome encapsulating a natural compound, wherein an average particle size (a median particle size) of the aquatic liposome encapsulating the natural compound ranges from 80 nm to 200 nm.

In an embodiment, the natural compound includes tetrahydrocurcumin (THC) or quercetin, and an effective amount of the natural compound encapsulated in the aquatic liposome ranges from 10 μM to 60 μM.

The present invention further provides a manufacturing method of an aquatic liposome encapsulating a natural compound, including: step S1: providing an aquatic liposome and mixing the aquatic liposome with the natural compound, wherein a mixed concentration of the aquatic liposome ranges from 0.05 mg/ml to 1.0 mg/ml; step S2: performing an ultrasonic oscillation after mixing the aquatic liposome and the natural compound, so that the natural compound is encapsulated in the aquatic liposome; and step S3: measuring the aquatic liposome, wherein an average particle size (a median particle size) of the aquatic liposome encapsulating the natural compound ranges from 80 nm to 200 nm.

The experiments conducted prove that the aquatic liposome encapsulating the natural compound (tetrahydrocurcumin (THC)) could effectively enter the microglia and the retinal pigment epithelium cells. When the microglia produce the inflammatory response due to the induction of *P. aeruginosa*, the aquatic liposome encapsulating the natural compound (tetrahydrocurcumin (THC)) entered the microglia could effectively reduce the inflammatory mediator levels of the inflammatory response. When the retinal pigment epithelium cells produce the lesion due to the induction of sodium iodate, the aquatic liposome encapsulating the natural compound (tetrahydrocurcumin (THC)) entered the retinal pigment epithelium cells could effectively reduce the reactive oxygen species level. Accordingly, the aquatic liposome encapsulating the natural compound (tetrahydrocurcumin (THC)) could suppress the inflammatory response and relieve the apoptosis of the retinal pigment epithelium cells, thereby preventing or treating eye-related inflammatory diseases or symptoms.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The present invention will be best understood by referring to the following detailed description of some illustrative embodiments in conjunction with the accompanying drawings, in which FIG. 1 is a flowchart of the manufacturing method of the aquatic liposome encapsulating the natural compound according to an embodiment of the present invention;

DETAILED DESCRIPTION OF THE INVENTION

Figure 2A:
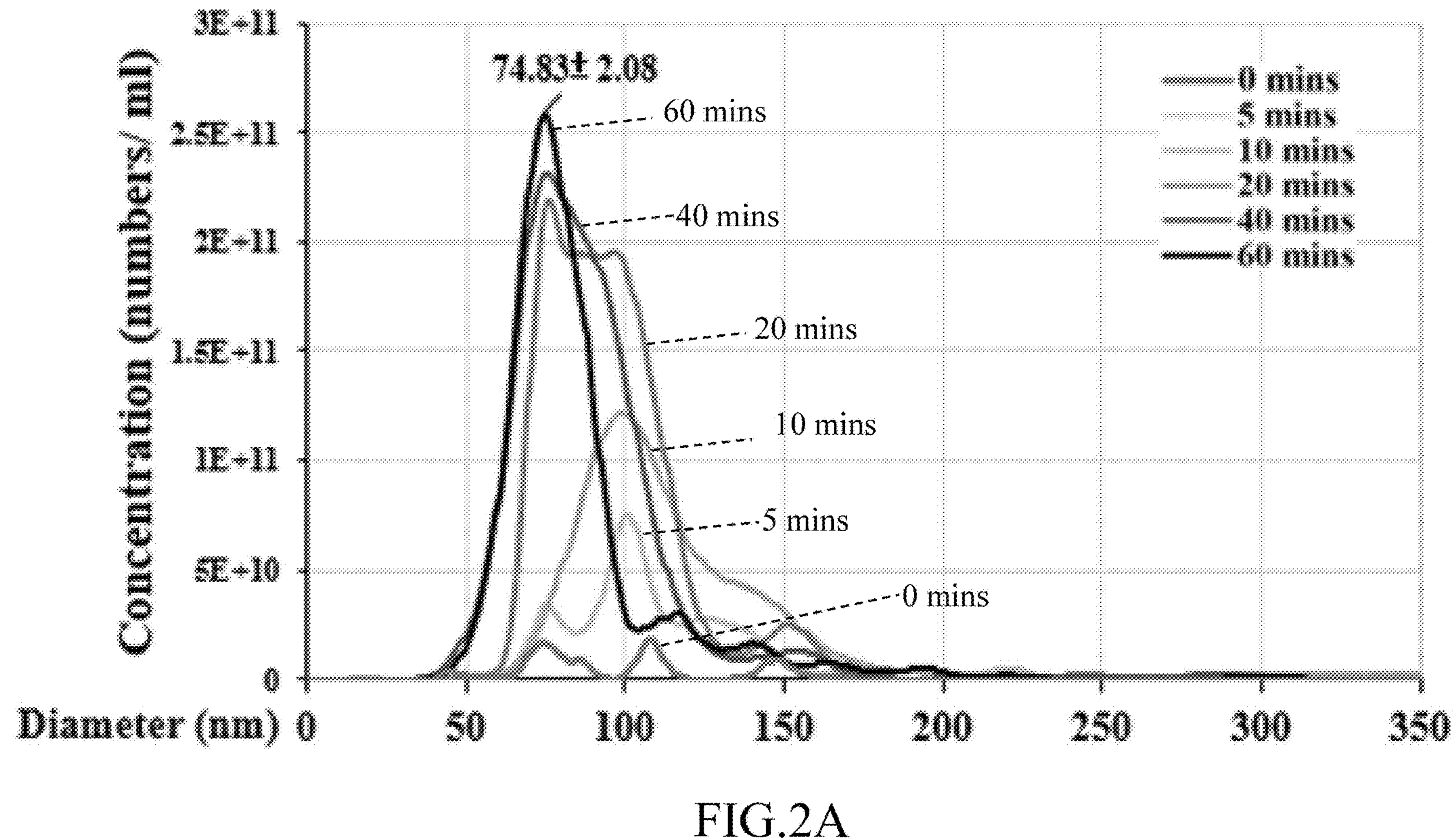
FIG. 2A is a diagram showing the average particle size of the aquatic liposomes at different oscillation times according to the embodiment of the present invention.

The present invention provides an embodiment of an aquatic liposome encapsulating a natural compound, wherein an average particle size (a median particle size) of the aquatic liposome encapsulating the natural compound ranges from 80 nm to 200 nm. In the current embodiment, the natural compound includes tetrahydrocurcumin (THC) or quercetin, and an effective amount of the natural compound encapsulated in the aquatic liposome ranges from 10 μM to 60 μM, but not limited thereto; the natural compound could be other drugs that could not directly enter cells. More specifically, in an embodiment, the aquatic liposome is obtained by extracting from fish skin of *Acipenser sinensis*, so that aquatic waste produced by processing the *Acipenser sinensis* could be consumed, thereby reducing the environmental pollution due to the aquatic waste. A process for the aquatic liposome to encapsulate the natural compound is to mix the aquatic liposome and the natural compound and then perform an ultrasonic oscillation on the aquatic liposome and the natural compound, wherein a mixed concentration of the aquatic liposome ranges from 0.05 mg/ml to 1.0 mg/ml. In an embodiment, the mixed concentration of the aquatic liposome ranges from 0.1 mg/ml to 0.5 mg/ml. In another embodiment, the mixed concentration of the aquatic liposome ranges from 0.2 mg/ml to 0.4 mg/ml. The aquatic liposome is recombined and polymerized due to the ultrasonic oscillation, so that the natural compound is encapsulated in the aquatic liposome during the recombination and polymerization of the aquatic liposome, thereby encapsulating the natural compound in the aquatic liposome. In the current embodiment, when the natural compound is tetrahydrocurcumin (THC), the average particle size (the median particle size) of the aquatic liposome encapsulating the tetrahydrocurcumin (THC) as measured ranges from 100 nm to 150 nm, but not limited thereto. In other embodiments, the aquatic liposome could encapsulate quercetin, and the average particle size (the median particle size) of the aquatic liposome encapsulating quercetin ranges from 100 nm to150 nm.

The current embodiment proves that the aquatic liposome with different concentrations affects an encapsulation efficiency of the aquatic liposome in encapsulating the natural compound. Use 0.05 to 1.0 mg/ml as the mixed concentration of the aquatic liposome, mix with tetrahydrocurcumin (THC) (50 μM) by ultrasonic oscillation, and the detect the encapsulation efficiency of the aquatic liposome. When the mixed concentration of the aquatic liposome ranges from 0.1 mg/ml to 0.5 mg/ml, the encapsulation efficiency of the aquatic liposome measured after the mixing and the ultrasonic oscillation of the aquatic liposome and the natural compound is greater than or equal to 50%, and the effective amount of the natural compound encapsulated in the aquatic liposome ranges from 12.5 μM to 50 μM. When the mixed concentration of the aquatic liposome ranges from 0.2 mg/ml to 0.4 mg/ml, the encapsulation efficiency of the aquatic liposome measured after the mixing and the ultrasonic oscillation of the aquatic liposome and the natural compound is greater than or equal to 65%, and the effective amount of the natural compound encapsulated by the aquatic liposome ranges from 25 μM to 50 μM. In an embodiment, the encapsulation efficiency of the aquatic liposome measured is greater than or equal to 80%.

A manufacturing method of the aquatic liposome encapsulating the natural compound of the aforementioned embodiment is explained below. Referring to FIG. 1, the manufacturing method of the aquatic liposome encapsulating the natural compound includes the following steps:

Step S1: provide an aquatic liposome and mix the aquatic liposome with the natural compound, wherein a mixed concentration of the aquatic liposome ranges from 0.05 mg/ml to 1.0 mg/ml;

Step S2: perform an ultrasonic oscillation after mixing the aquatic liposome and the natural compound, wherein a frequency of the ultrasonic oscillation ranges from 30 kHz to 50 kHz and an oscillation time is between 5 min and 60 min; in an embodiment, the frequency of the ultrasonic oscillation is 40 kHz, and the oscillation time ranges from 20 min to 60 min; in this way, the natural compound is encapsulated in the aquatic liposome;

Step S3: measure the aquatic liposome, wherein an average particle size (a median particle size) of the aquatic liposome encapsulating the natural compound ranges from 80 nm to 200 nm; in the current embodiment, multiple experiments are conducted to prove that the natural compound (tetrahydrocurcumin (THC)) with the particular effective amount that is encapsulated in the aquatic liposome could effectively enter microglia and retinal pigment epithelium cells.

The term “effective amount” as referred to herein is an amount of an active ingredient in a composition which is sufficient to produce a desired physiological response. The effective amount of the active ingredient does not necessarily cure a disease or a symptom but could slow, stop, prevent, or relieve the development of the symptom. The actual effective amount of the active ingredient depends on many factors, such as particular the condition of experiment, the physiological condition of subjects (e.g., weight, age, gender), the type of subjects undertaking the experiments, the duration of the experiments, the actual formula used. For example, the effective amount of the active ingredient could be expressed in concentration, such as molar concentration, weight concentration, volume concentration, mole fraction, mass fraction, and mixing ratio. One of ordinary skill in the art could calculate the human equivalent dose (HED) for human medication based on doses determined from animal models.

The concentration ratio in the manufacturing method of the aquatic liposome encapsulating the natural compound in the current embodiment is not a limitation of the present invention. The parameters that could be appropriately adjusted by one of ordinary skill in the art after referring the present invention should still fall within the scope of the present invention.

In order to demonstrate the purpose, the features, and the effects of the present invention, characteristic analysis of the aquatic liposome before and after encapsulating tetrahydrocurcumin (THC) according to the current embodiment of the present invention, measurement of the encapsulation efficiency of the aquatic liposome, determination of the anti-inflammatory effect of tetrahydrocurcumin (THC) with different effective amounts, and determination of the effect of tetrahydrocurcumin (THC) with different effective amounts in suppressing the apoptosis are conducted.

Experimental Materials:

Reagents:

Tetrahydrocurcumin (THC) (no.: sc-391609) is from Santa Cruz (US). Cell-permeable fluorescent probe H2DCFH-DA (2',7'-dichlorodihydro-fluorescein diacetate) (no.: 15204) is from AAT bioquest (US). Cell Counting Kit-8 (CCK-8) is from Dojindo Molecular Technologies (US). Annexin V and propidium iodide (PI) are from Thermo Fisher (US).

The aquatic liposome (abbreviation: Asl-lipo) is obtained from 50 g of *Acipenser sinensis* skin in the market; the *Acipenser sinensis* skin and 950 mL of 95% ethanol are placed in a blender for evenly blending over 5 minutes to form a mixture; the mixture is placed in an ultrasonic machine (D200H) at 70° C. for oscillation over 1 hour; then, ethanol and most of the impurities of the *Acipenser sinensis* skin in the mixture are filtered by a filter funnel; ethanol is removed and subsequent drying is performed by a rotary evaporator; then 50 mL of acetone is added to form an acetone mixture; the acetone mixture is left to react overnight at −20° C.; the rotary evaporator is from Buchi Rotavapor Rii (Australia); after the reaction is completed, centrifugation at 3000 g is performed on the acetone mixture at 0° C. for 5 minutes; then a supernatant is removed; another 50 mL of acetone is added for another rinsing and another centrifugation is performed; another supernatant is removed; after residual acetone is evaporated, a precipitate is dissolved in an anhydrous ethanol to form an anhydrous ethanol mixture; the anhydrous ethanol mixture is stored a −20° C. to prevent oxidation of lipid; after ethanol in the anhydrous ethanol mixture is evaporated, a dried phospholipid is weighted; the dried phospholipid is redissolved in phosphate buffered saline (PBS) or double-distilled water ($d_2H_2O$); then an aggregated phospholipid precipitate is broken down by a tube shaker (model: Vortex-Genie 2, SI-0235), wherein the tube shaker (model: Vortex-Genie 2, SI-0235) is from Scientific Industries (US); afterwards, the ultrasonic oscillation is performed again (an oscillation frequency is 40 kHz) to obtain the aquatic liposome.

1. Determination of the Characteristics of the Aquatic Liposome

How an oscillation time of the ultrasonic oscillation correspondingly affects a distribution of a particle size of the aquatic liposome (Asl-lipo) is determined. The particle size of the aquatic liposome is measured by NanoSight NS3000. The measuring procedure includes the following steps: perform a device calibration by using standardized samples of 100 nm and 200 nm; then a 1 ml syringe is filled with a sample of the aquatic liposome and no bubble is produced; the syringe is connected to a transferring tube and a micro-injection pump; the micro-injection pump is set to transfer the sample of the aquatic liposome at 25 μL/min at 25° C.; the aforementioned step is performed three times for measuring the particle size of the aquatic liposome and each time last 60 seconds. NanoSight NS3000 is to detect nanoparticles of the aquatic liposome passing through the transferring tube to enter the 0.25 ml chamber with the setting of the absorption wavelength of 635 nm and the shutter speed of 15 ms. The detection result of the nanoparticles of the aquatic liposome is analyzed by NTA2.1 software (Nanosight). An average particle size and a median particle size of the aquatic liposome (Asl-lipo) are calculated, and the number of particles at different concentrations is calculated based on the dilution factor.

The current experiment is to perform the ultrasonic oscillation at different oscillation times on the aquatic liposome (Asl-lipo), wherein the oscillation times of the ultrasonic oscillation (the oscillation frequency is set 40 kHz) are set 0 min, 5 min, 10 min, 20 min, 40 min, and 60 min, respectively. The average particle size (nm) and the polydispersity index (PDI) of the aquatic liposome (Asl-lipo) in correspondence with the different oscillation times are measured.

The result of the experiment is shown in FIG. 2A and Table 1. When the oscillation time of ultrasonic oscillation is 0 min (only by vortex mixer), the average particle size (nm) of the aquatic liposome (Asl-lipo) measured is $101.53 \pm 26.80$ nm$^{b,c}$ and the polydispersity index (PDI) is $0.315 \pm 0.030^{a}$. When the oscillation time of the ultrasonic oscillation is 5 min, the average particle size (nm) of the aquatic liposome (Asl-lipo) measured is 111.30±32.10 nm$^{b}$ and the polydispersity index (PDI) is 0.247±0.73$^{a,b}$. When the oscillation time of ultrasonic oscillation is 10 min, the average particle size (nm) of the aquatic liposome (Asl-lipo) measured is 133.30±53.60 nm$^{a}$ and the polydispersity index (PDI) is 0.162±0.048$^{b}$. When the oscillation time of ultrasonic oscillation is 20 min, the average particle size (nm) of the aquatic liposome (Asl-lipo) measured is 97.63±28.50 nm$^{b,c}$ and the polydispersity index (PDI) is 0.087±0.024$^{c}$. When the oscillation time of ultrasonic oscillation is 40 min, the average particle size (nm) of the aquatic liposome (Asl-lipo) measured is 88.78±27.88 nm$^{c}$ and the polydispersity index (PDI) is 0.099±0.019$^{c}$. When the oscillation time of ultrasonic oscillation is 60 min, the average particle size (nm) of the aquatic liposome (Asl-lipo) measured is 89.60±30.73 nm$^{c}$ and the polydispersity index (PDI) is 0.097±0.018$^{c}$.

The result of the experiment shows that when the oscillation time of the ultrasonic oscillation is above 20 min, the polydispersity index (PDI) of the aquatic liposome (Asl-lipo) is lowered to be less than 0.1, and the average particle size of the aquatic liposome (Asl-lipo) is less than 100 nm, indicating that the oscillation time of the ultrasonic oscillation affects the average particle size (nm) and the polydispersity index (PDI) of the aquatic liposome (Asl-lipo).

TABLE 1

Table 1 is a data table of the average particle size (nm) and the polydispersity index (PDI) of the aquatic liposome (Asl-lipo) measured in correspondence with different oscillation times of the ultrasonic oscillation.

| Oscillation time (min) | Average particle size (nm) | Polydispersity index (PDI) |
|---|---|---|
| 0 | 101.53 ± 26.80$^{b,\ c}$ | 0.315 ± 0.030$^{a}$ |
| 5 | 111.30 ± 32.10$^{b}$ | 0.247 ± 0.73$^{a,\ b}$ |
| 10 | 133.30 ± 53.60$^{a}$ | 0.162 ± 0.048$^{b}$ |
| 20 | 97.63 ± 28.50$^{b,\ c}$ | 0.087 ± 0.024$^{c}$ |
| 40 | 88.78 ± 27.88$^{c}$ | 0.099 ± 0.019$^{c}$ |
| 60 | 89.60 ± 30.73$^{c}$ | 0.097 ± 0.018$^{c}$ |

Different letters (a-c) superscripted in the statistical chart and the description indicate that there is statistical significance between groups ($p<0.05$); on the contrary, being marked with the same letter indicates that there is no statistical significance.

The influence of the oscillation time of the ultrasonic oscillation on the particle distribution of the aquatic liposome (Asl-lipo) is determined. The current experiment is to similarly perform the ultrasonic oscillation on the aquatic liposome (Asl-lipo), wherein the oscillation times of the ultrasonic oscillation (the oscillation frequency is set 40 kHz) are set 0 min, 5 min, 10 min, 20 min, 40 min, and 60 min, respectively. The difference in the distribution of the aquatic liposome (Asl-lipo) with the particle size less than 200 nm in correspondence with different oscillation times are analyzed. The current experiment divides the average particle size (nm) of the aquatic liposome (Asl-lipo) into four groups, including 0-50 nm, 50-100 nm, 100-150 nm, and 150-200 nm. The distribution of the aquatic liposome (Asl-lipo) within the four groups are summarized.

Figure 2B:
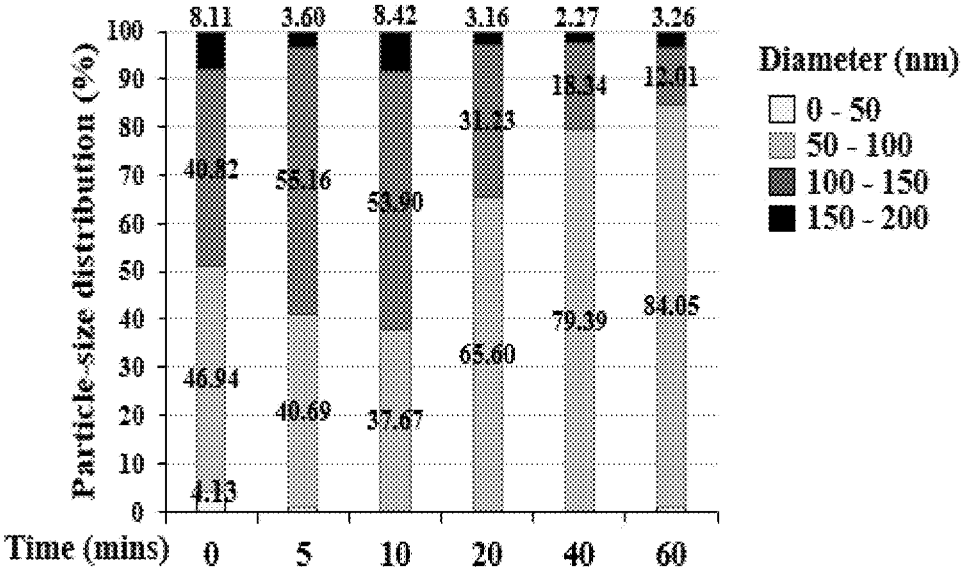
FIG. 2B is a diagram showing the particle size distribution of the aquatic liposomes at different oscillation times according to the embodiment of the present invention.

The result of the experiment is shown in FIG. 2B. When no ultrasonic oscillation is performed on the aquatic liposome (Asl-lipo) (the oscillation time is 0 min), the particle size of the aquatic liposome (Asl-lipo) is more dispersed, wherein a measured number of the aquatic liposome (Asl-lipo) in the group with the particle size of 0-50 nm is 4.13±2.36%; a measured number of the aquatic liposome (Asl-lipo) in the group with the average particle size of 50-100 nm is 46.94±35.61%; a measured number of the aquatic liposome (Asl-lipo) in the group with the average particle size of 100-150 nm is 40.82±38.19%; a measured number of the aquatic liposome (Asl-lipo) in the group with the average particle size of 150-200 nm is 8.11±14.12%. When the oscillation time of the ultrasonic oscillation is greater than or equal to 20 min, the proportion of the average particle size (nm) of the aquatic liposome (Asl-lipo) measured to be between 50-100 nm could be greater than or equal to 65%.

It should be noted that when the oscillation time of the ultrasonic oscillation on the aquatic liposome (Asl-lipo) was 5 min, the measured particle size of the aquatic liposome was 40.69% with a particle size of 50-100 nm, and the amount with the particle size of 100-150 nm is 55.16%. When the oscillation time of the ultrasonic oscillation on the aquatic liposome (Asl-lipo) was 10 min, the measured particle size of the aquatic liposome was 37.67% with a particle size of 50-100 nm, and the amount with the particle size of 100-150 nm is 53.9% When the oscillation time of the ultrasonic oscillation on the aquatic liposome (Asl-lipo) is increased to 20 min or above (40 min and 60 min), the polydispersity index (PDI) of the aquatic liposome (Asl-lipo) in each group of the particle size is decreased. The particle size of the aquatic liposome (Asl-lipo) in each group of the particle size steadily falls within 50-100 nm, wherein the measured number of the aquatic liposome Asl-lipo ranges from 65.6% to 84.04%.

Figure 2C:
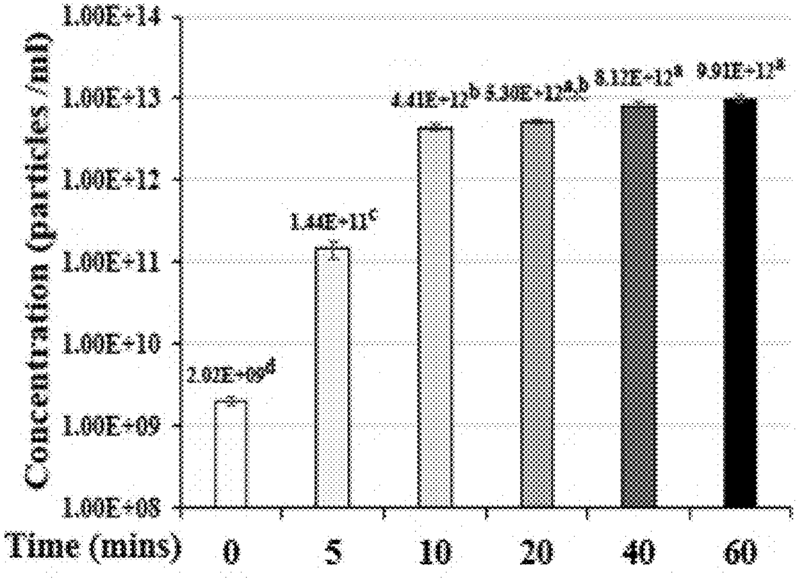
FIG. 2C is a diagram showing the number of the particles of the aquatic liposomes at different oscillation times according to the embodiment of the present invention.

Moreover, the number of particles formed in correspondence with different oscillation times of the ultrasonic oscillation is analyzed. The result of the experiment is shown in FIG. 2C. When no ultrasonic oscillation is performed on the aquatic liposome (Asl-lipo) (the oscillation time is 0 min), a measured value of the aquatic liposome (Asl-lipo) is $2.02\pm0.22\times10^{9}$ (particles/ml). When the oscillation time of the ultrasonic oscillation on the aquatic liposome (Asl-lipo) is 5 min, the measured value of the aquatic liposome (Asl-lipo) is $1.44\pm0.35\times10^{11}$. When the oscillation time of the ultrasonic oscillation on the aquatic liposome (Asl-lipo) is 10 min, the measured value of the aquatic liposome (Asl-lipo) is $4.41\pm0.33\times10^{12}$. When the oscillation time of the ultrasonic oscillation on the aquatic liposome (Asl-lipo) is 20 min, the measured value of the aquatic liposome (Asl-lipo) is $5.30\pm0.33\times10^{12}$. When the oscillation time of the ultrasonic oscillation on the aquatic liposome (Asl-lipo) is 40 min, the measured value of the aquatic liposome (Asl-lipo) is $8.12\pm0.33\times10^{12}$. When the oscillation time of the ultrasonic oscillation on the aquatic liposome (Asl-lipo) is 60 min, the measured value of the aquatic liposome (Asl-lipo) is $9.91\pm0.33\times10^{12}$.

The aforementioned experiment shown that the oscillation time of the ultrasonic oscillation significantly influences the particle size, the particle size distribution, and the number of particles formed of the aquatic liposome (Asl-lipo). When the oscillation time of the ultrasonic oscillation on the aquatic liposome (Asl-lipo) is 10-60 min, the stability of the particle size distribution of the aquatic liposome (Asl-lipo) could be effectively enhanced, so that the average particle size of the aquatic liposome (Asl-lipo) is within 50-100 nm and the number of particles formed of the aquatic liposome (Asl-lipo) with the particle size of 50-100 nm is relatively increased.

2. Determination of the Encapsulation Efficiency (EE) of the Aquatic Liposome (Asl-lipo) in Encapsulating Tetrahydrocurcumin (THC)

The current experiment includes the following steps: the aquatic liposome (Asl-lipo) is prepared to have a mixed concentration of 0.05 mg/ml, 0.1 mg/ml, 0.2 mg/ml, 0.4 mg/ml, 0.6 mg/ml, 0.8 mg/ml, and 1.0 mg/ml respectively; an effective amount of tetrahydrocurcumin (THC) is 50 μM; each group of the aquatic liposome (Asl-lipo) (0.05 mg/ml, 0.1 mg/ml, 0.2 mg/ml, 0.4 mg/ml, 0.6 mg/ml, 0.8 mg/ml, and 1.0 mg/ml) is mixed with the same volume of tetrahydrocurcumin (THC); the ultrasonic oscillation is performed for 60 min (the oscillation frequency is 40 kHz) to evenly mix the aquatic liposome (Asl-lipo) and tetrahydrocurcumin (THC); an initial particle number is calculated by NTA.

Calculation with NTA is to firstly withdraw 500 μl of the mixed solution and add the mixed solution to 10 ml of $d_2H_2O$; after mixing evenly, ultracentrifugation at 100000 rpm is performed for 90 min; the supernatant is removed and then 500 μl of $d_2H_2O$ is added for redissolving; the liposome is collected and the particle number collected is calculated by NTA; the collection rate of the liposome is calculated based on [the particle number collected/the initial particle number]. Afterwards, a polyphenolic compound content in the liposome is analyzed by Folin-Ciocalteu method. A relative content is calculated by comparing the standard curve of tetrahydrocurcumin (THC) through interpolation. An encapsulation concentration of tetrahydrocurcumin (THC) is calculated based on [the relative content of tetrahydrocurcumin (THC)/the collection rate]. A drug encapsulation efficiency of the tetrahydrocurcumin (THC) is calculated based on [the encapsulation concentration of tetrahydrocurcumin (THC)/an initial tetrahydrocurcumin (THC) concentration (50 μM)].

In the current experiment, the quantitation of the polyphenolic compound is to obtain 50 μL of samples and the samples are respectively added to a glass tube; after evenly mixing with 1 mL of IN Folin-Ciocalteu's phenol regent and 1 mL of 7.5% sodium carbonate solution, a resulted solution is left at room temperature for 5 min; afterward, 4,500 μL of 20% sodium carbonate solution is added; after ultrasonic oscillation is performed, the resulted solution is left at room temperature for 10 min; centrifugation at 3000 rpm is performed for 10 min; the supernatant is withdrawn and the 735 nm absorbance of the supernatant is measured by UV-visible spectrophotometer (T-90 Spectrophotometer from PG Instruments Limited). The greater the absorbance, the greater the phenolic compound content. To determine the drug encapsulation efficiency, the phenolic compound content of the current experiment is calculated by calculating a relative content of tetrahydrocurcumin (THC) in the sample while comparing the standard curve of tetrahydrocurcumin (THC).

Figure 3A:
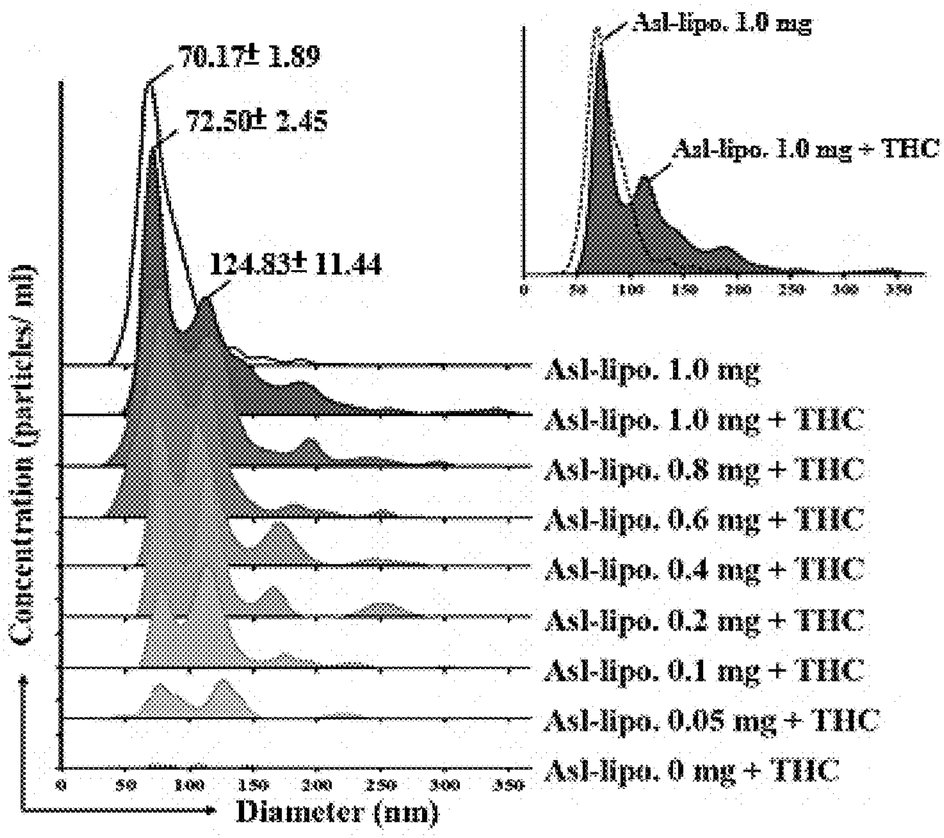
FIG. 3A is a diagram showing the distribution of the particles of the aquatic liposomes at different oscillation times according to the embodiment of the present invention.

The result of the experiment is shown in FIG. 3A. When the mixed concentration of the aquatic liposome (Asl-lipo) is 1.0 mg/ml (without adding tetrahydrocurcumin (THC)), the particle size of the aquatic liposome (Asl-lipo) is 50-100 nm and the peak(s) is(are) 70.17±1.89 nm. When the ultrasonic oscillation is performed on the aquatic liposome (Asl-lipo) (0.05 mg/ml, 0.1 mg/ml, 0.2 mg/ml, 0.4 mg/ml, 0.6 mg/ml, 0.8 mg/ml, and 1.0 mg/ml) and tetrahydrocurcumin (THC), the particle size of a part of the aquatic liposome (Asl-lipo) falls within 50-100 nm and 100-150 nm, indicating that the average particle size (the median particle size) of the aquatic liposome (Asl-lipo) encapsulating tetrahydrocurcumin (THC) is 100-150 nm.

Figure 3B:
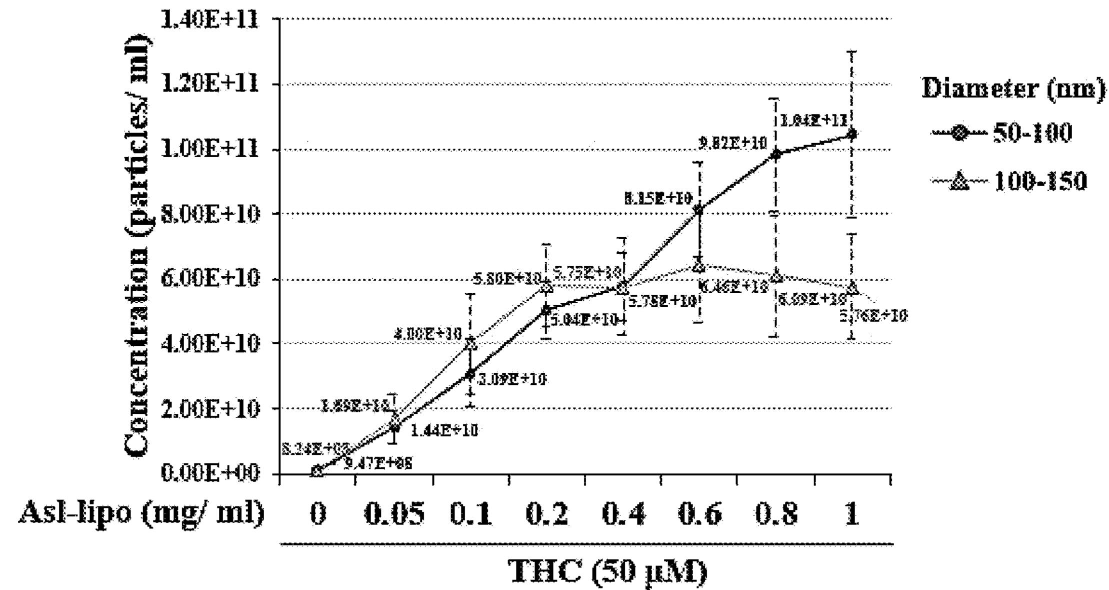
FIG. 3B is a diagram showing the encapsulation efficiency of the aquatic liposomes encapsulating tetrahydrocurcumin (THC) at different oscillation times according to the embodiment of the present invention.

The actual particle numbers of the aquatic liposome (Asl-lipo) encapsulating tetrahydrocurcumin (THC) and with the particle size of 50-100 nm and 100-150 nm are calculated. The result of the experiment is shown in FIG. 3B. The number of particles encapsulating tetrahydrocurcumin (THC) by the aquatic liposome (Asl-lipo) increases with the mixed concentration of the aquatic liposome (Asl-lipo), leading to an increase in the number of particles with a diameter of 50-100 nm. In contrast, when the mixed concentration of the aquatic liposome (Asl-lipo) exceeds 0.2 mg/ml (including 0.4 mg/ml, 0.6 mg/ml, 0.8 mg/ml, and 1.0 mg/ml), the number of particles encapsulating tetrahydrocurcumin (THC) with a diameter of 100-150 nm does not increase with the increase in the mixed concentration of the aquatic liposome (Asl-lipo). It shows that the saturation point has been reached when the mixed concentration of the aquatic liposome (Asl-lipo) reaches 0.4 mg/ml. Accordingly, when the aquatic liposome (Asl-lipo) with the mixed concentration of 0.05 mg/ml, 0.1 mg/ml, and 0.2 mg/ml is mixed with tetrahydrocurcumin (THC), a good encapsulation efficiency could be provided, wherein when the mixed concentration of the aquatic liposome (Asl-lipo) is 0.1 mg/ml or 0.2 mg/ml, the better encapsulation efficiency in encapsulating tetrahydrocurcumin (THC) could be achieved.

Moreover, to determine that the ability of the aquatic liposome (Asl-lipo) in encapsulating tetrahydrocurcumin (THC), the polyphenolic compound content of the aquatic liposome (Asl-lipo) (0.05 mg/ml, 0.1 mg/ml, 0.2 mg/ml, 0.4 mg/ml, 0.6 mg/ml, 0.8 mg/ml, and 1.0 mg/ml) encapsulating tetrahydrocurcumin (THC) is measured by Folin-Ciocalteu method. After comparing with the standard curve of tetrahydrocurcumin (THC; 50 μM), the relative tetrahydrocurcumin (THC) content and the encapsulation efficiency (EE) of encapsulating tetrahydrocurcumin (THC) are calculated.

Figure 4A:
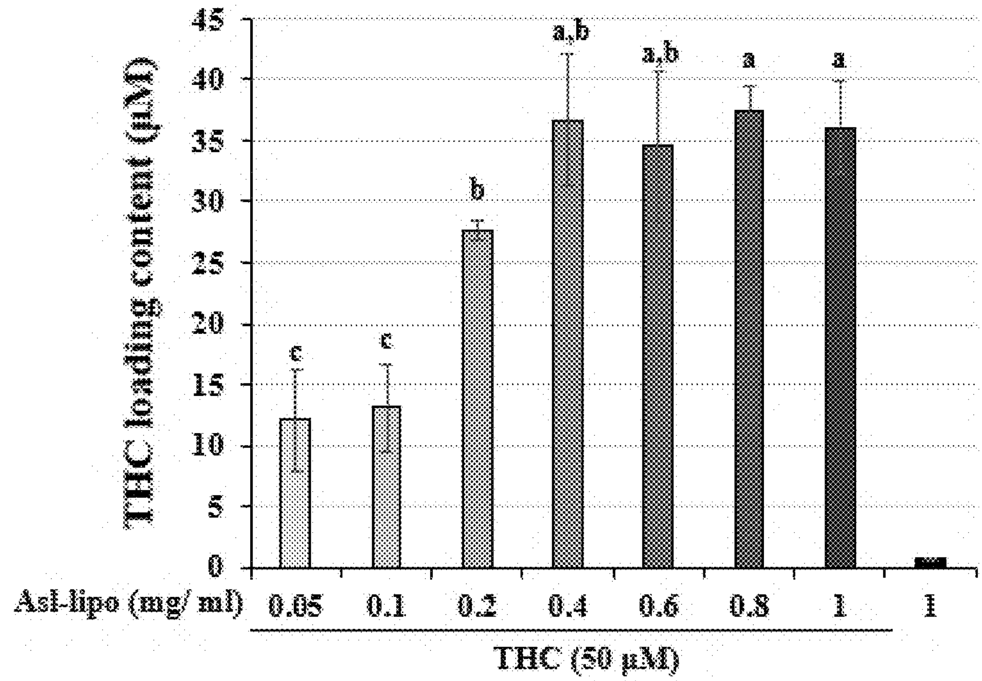
FIG. 4A is a diagram showing the distribution of the aquatic liposomes encapsulating tetrahydrocurcumin (THC) at different concentrations of the aquatic liposomes according to the embodiment of the present invention.
Figure 4B:
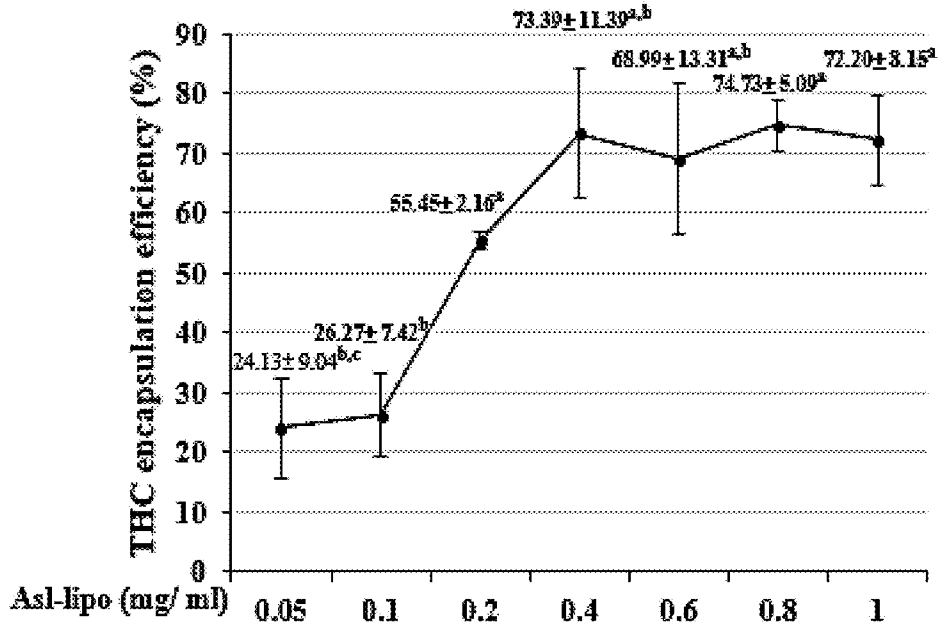
FIG. 4B is a diagram showing the encapsulation efficiency of the aquatic liposomes encapsulating tetrahydrocurcumin (THC) at different concentrations of the aquatic liposomes according to the embodiment of the present invention.

The result of the experiment is shown in FIG. 4A and FIG. 4B. When the mixed concentration of the aquatic liposome (Asl-lipo) is equal to or less than 0.2 mg/ml (including 0.05 mg/ml, 0.1 mg/ml, and 0.2 mg/ml), the tetrahydrocurcumin (THC) content encapsulated in the aquatic liposome (Asl-lipo) increases with the increase in the mixed concentration of the aquatic liposome (Asl-lipo). When the mixed concentration of the aquatic liposome (Asl-lipo) is 0.4 mg/ml, the tetrahydrocurcumin (THC) content reaches a saturated state, and the encapsulation efficiency (EE) of the aquatic liposome (Asl-lipo) with the mixed concentration of 0.4 mg/ml is 73.39±11.39% (shown in FIG. 4B). Accordingly, the combination of the aquatic liposome (Asl-lipo) with the mixed concentration of 0.4 mg/ml and the 50 μM tetrahydrocurcumin (THC) is the maximum working dose for the subsequent experiment.

3. Determination of the Capability of the Aquatic Liposome (Asl-lipo) in Encapsulating Drug The current experiment is to determine the aquatic liposome's (Asl-lipo) capability in encapsulating other drugs. The current experiment includes the following steps: the aquatic liposome (Asl-lipo) is dissolved in phosphate buffered saline (PBS); then two dyes that cannot directly enter cells, including Annexin V and Propidium iodide (PI), are respectively added to the aquatic liposome (Asl-lipo); mixing is performed through the ultrasonic oscillation, while no ultrasonic oscillation is performed on a control group; after adding Annexin V and Propidium iodide (PI) to the aquatic liposome (Asl-lipo) for reacting over 2 hours, a mixture is observed by using a fluorescence microscope. In the experiment of the permeability of the aquatic liposome (Asl-lipo), it can be seen from the aforementioned experiment and analysis of the encapsulation efficiency that when a mass ratio of the aquatic liposome (Asl-lipo) (the mixed concentration is 0.2 mg/ml) to tetrahydrocurcumin (THC) (50 μM, MW=374.12) is 10:1, the maximum encapsulation efficiency of the aquatic liposome (Asl-lipo) could be achieved. The cells of the current experiment are retinal pigment epithelium cells (ARPE-19) provided by professors in Chung Shan Medical University.

More specifically, the current experiment is to perform Annexin V and Propidium iodide (PI) test on three groups of the retinal pigment epithelium cells (ARPE-19): (1) Mock: only 20 μg/ml of PI is added (FIG. 5A) or only 20 μg/ml of Annexin V is added (FIG. 6A); (2) Control group: the aquatic liposome (Asl-lipo) is mixed with 20 μg/ml of PI without the ultrasonic oscillation, and the mixture of the aquatic liposome (Asl-lipo) and PI is mixed with the retinal pigment epithelium cells (ARPE-19) (FIG. 5A); the aquatic liposome (Asl-lipo) is mixed with 20 μg/ml of Annexin V without the ultrasonic oscillation, and the mixture of the aquatic liposome (Asl-lipo) and Annexin V is added to the retinal pigment epithelium cells (ARPE-19) (FIG. 6A); (3) Experimental group: the aquatic liposome (Asl-lipo) is mixed with 20 μg/ml of PI and the ultrasonic oscillation at 40 kHz is performed for 20 min; then the mixture of the aquatic liposome (Asl-lipo) and PI is added to the retinal pigment epithelium cells (ARPE-19) (FIG. 5A); the aquatic liposome (Asl-lipo) is mixed with 20 μg/ml of Annexin V and the ultrasonic oscillation at 40 kHz is performed for 20 min; then the mixture of the aquatic liposome (Asl-lipo) and Annexin V is added to the retinal pigment epithelium cells (ARPE-19) (FIG. 6A). After the reaction is completed, the mock, the control group, and the experimental group are respectively rinsed with phosphate buffered saline (PBS). Green fluorescence images at 490~525 nm (Annexin V-FITC), red fluorescence images at 590 nm (PI), and blue images at 350~460 nm (DAPI) of the mock, the control group, and the experimental group are taken by the upright fluorescence microscope (Zeiss Axio Imager. A1, Jena, Germany), and fluorescence quantitation is performed by Image J (National Institutes of Health, Bethesda, MD, USA).

Figure 5A:
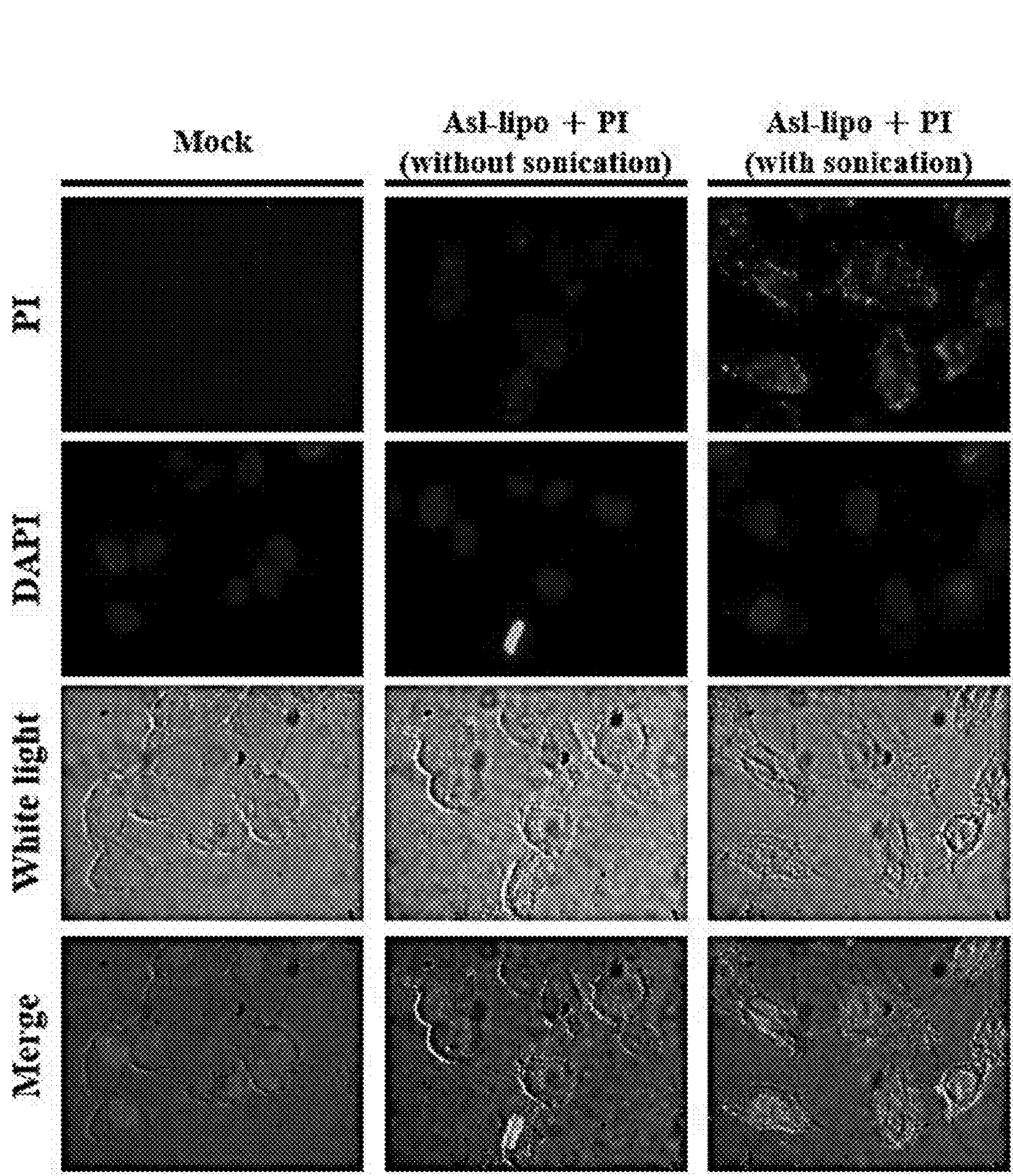
FIG. 5A is a diagram showing the aquatic liposomes encapsulating propidium iodide (PI) according to the embodiment of the present invention.
Figure 5B:
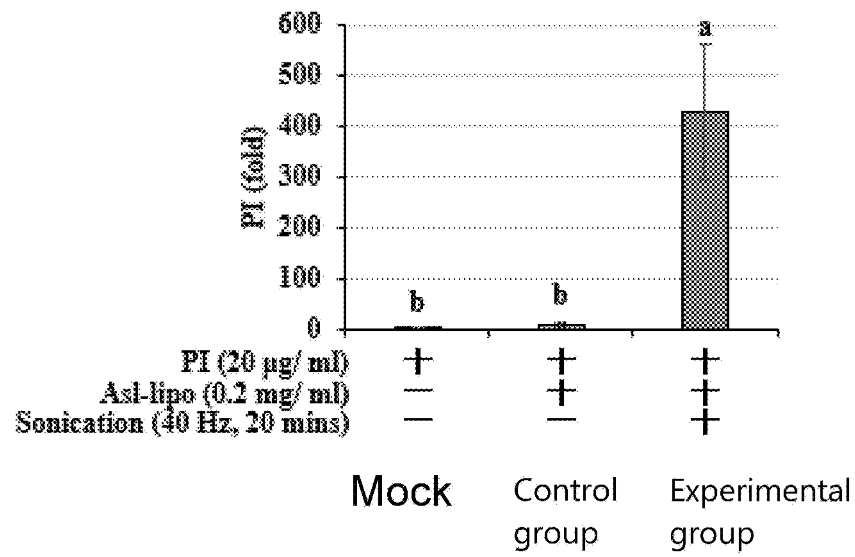
FIG. 5B is a diagram showing the cell permeability of the aquatic liposomes encapsulating propidium iodide (PI) according to the embodiment of the present invention.
Figure 6A:
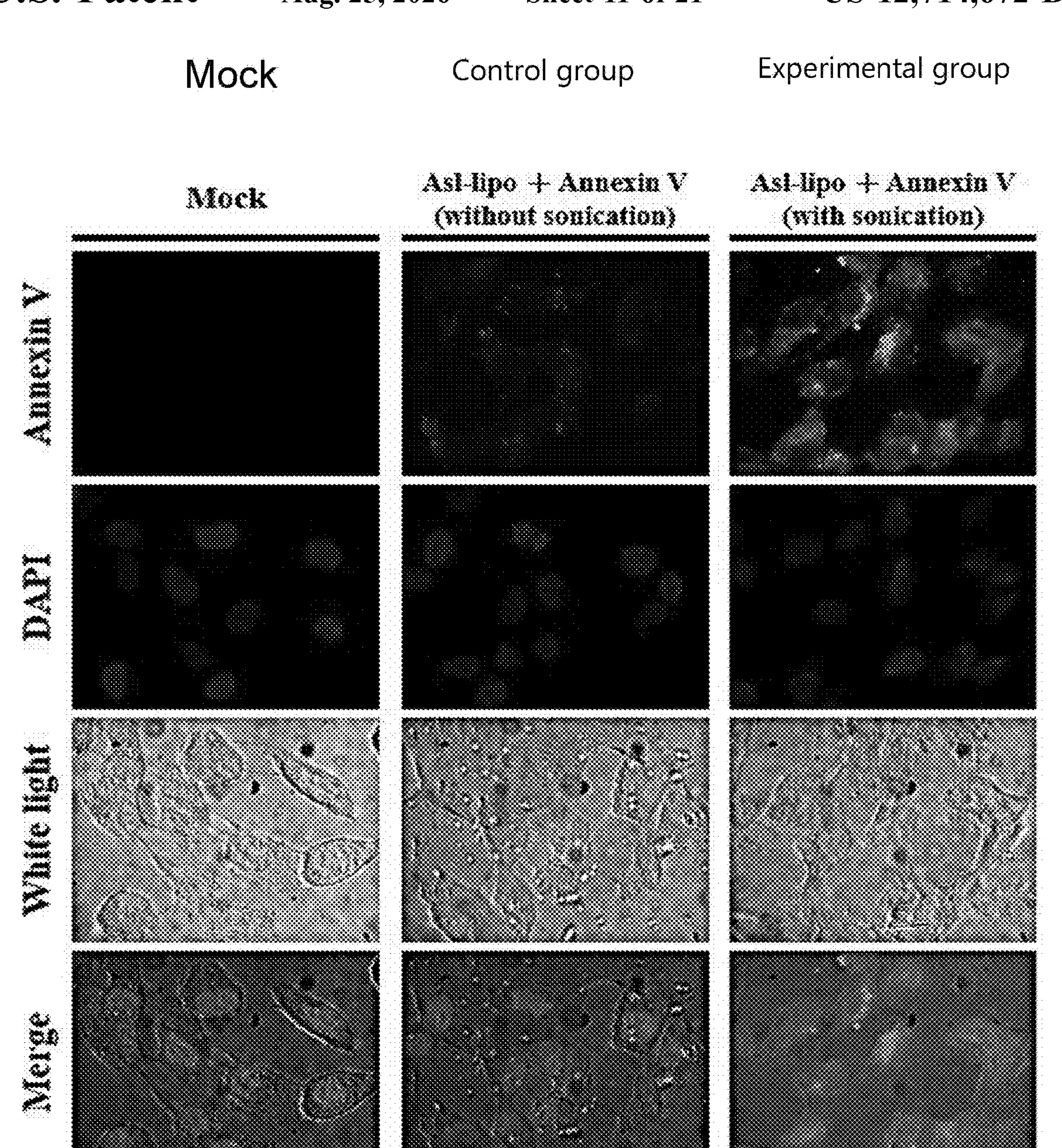
FIG. 6A is a diagram showing the aquatic liposomes encapsulating Annexin V according to the embodiment of the present invention.
Figure 6B:
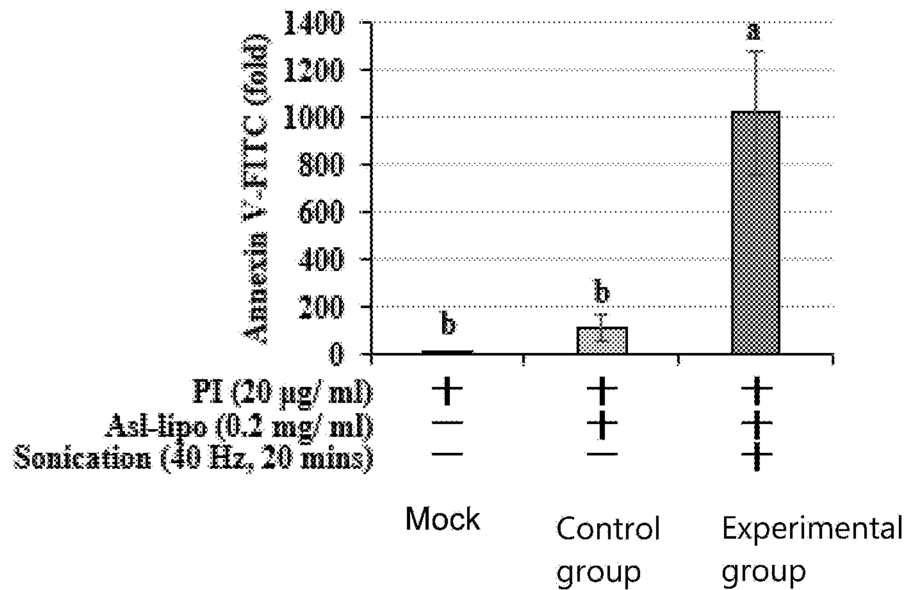
FIG. 6B is a diagram showing the cell permeability of the aquatic liposomes encapsulating Annexin V according to the embodiment of the present invention.

Referring to the result of the experiment shown in FIG. 5A and FIG. 5B, the aquatic liposome (Asl-lipo) in the experimental group could effectively encapsulate PI and transport PI into the retinal pigment epithelium cells (ARPE-19). Referring to the result of the experiment shown in FIG. 6A and FIG. 6B, the experimental group's aquatic liposome (Asl-lipo) could effectively encapsulate Annexin V and transport Annexin V into the retinal pigment epithelium cells (ARPE-19).

4. Determination of the Anti-Inflammatory Effect of the Aquatic Liposome (Asl-lipo) Encapsulating Tetrahydrocurcumin (THC)

Figure 7A:
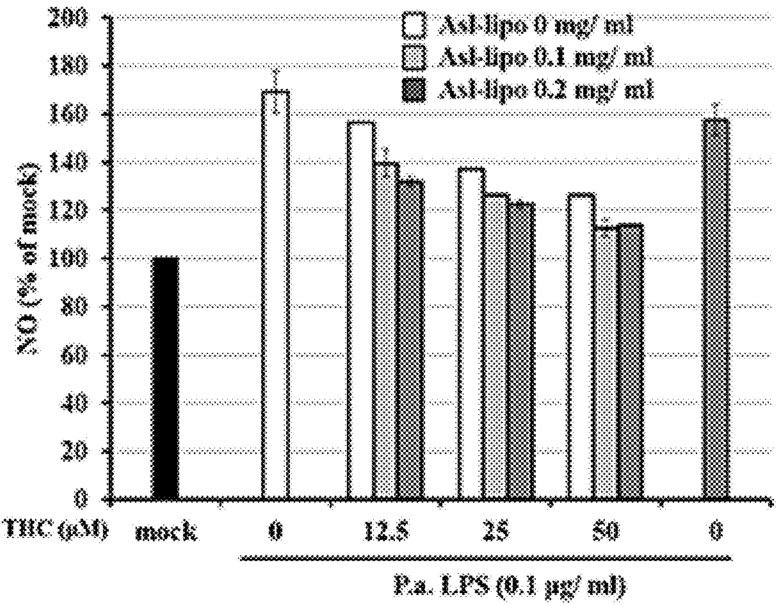
FIG. 7A is a diagram showing the relationship between the concentration of the aquatic liposomes encapsulating tetrahydrocurcumin (THC) and the concentration of nitrite produced by the microglia (BV-2) due to the induction of *P. aeruginosa* according to the embodiment of the present invention.
Figure 7B:
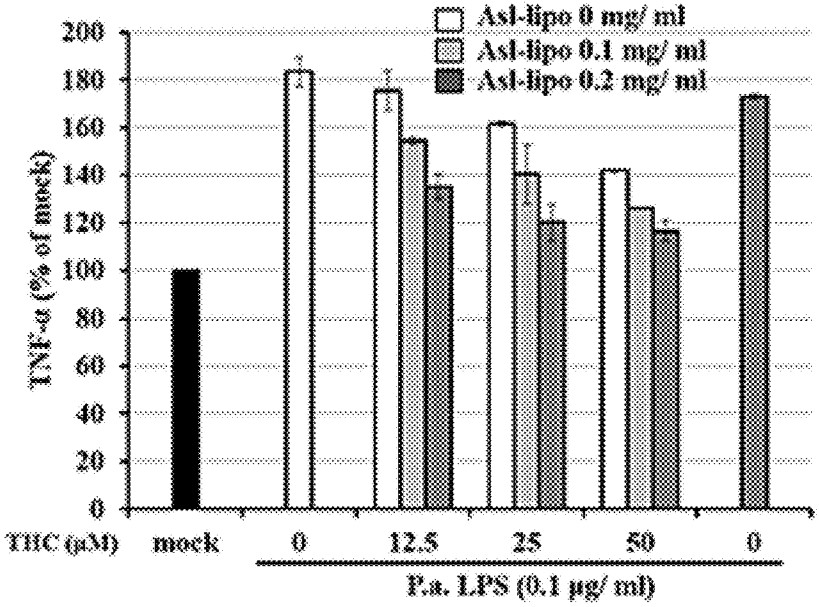
FIG. 7B is a diagram showing the relationship between the concentration of the aquatic liposomes encapsulating tetrahydrocurcumin (THC) and the concentration of the cytokine TNF-$\alpha$ produced by the microglia (BV-2) due to the induction of *P. aeruginosa* according to the embodiment of the present invention.
Figure 7C:
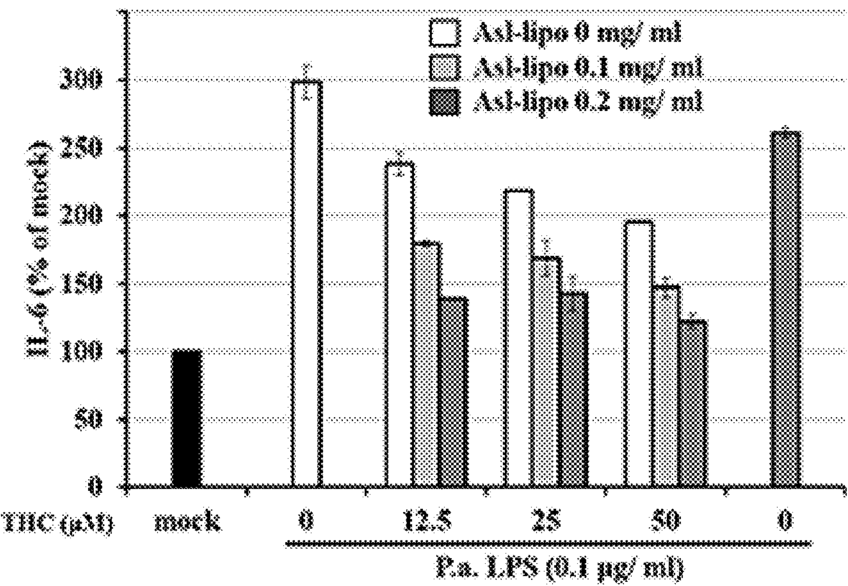
FIG. 7C is a diagram showing the relationship between the concentration of the aquatic liposomes encapsulating tetrahydrocurcumin (THC) and the concentration of the cytokine IL-6 produced by the microglia (BV-2) due to the induction of *P. aeruginosa* according to the embodiment of the present invention.
Figure 7D:
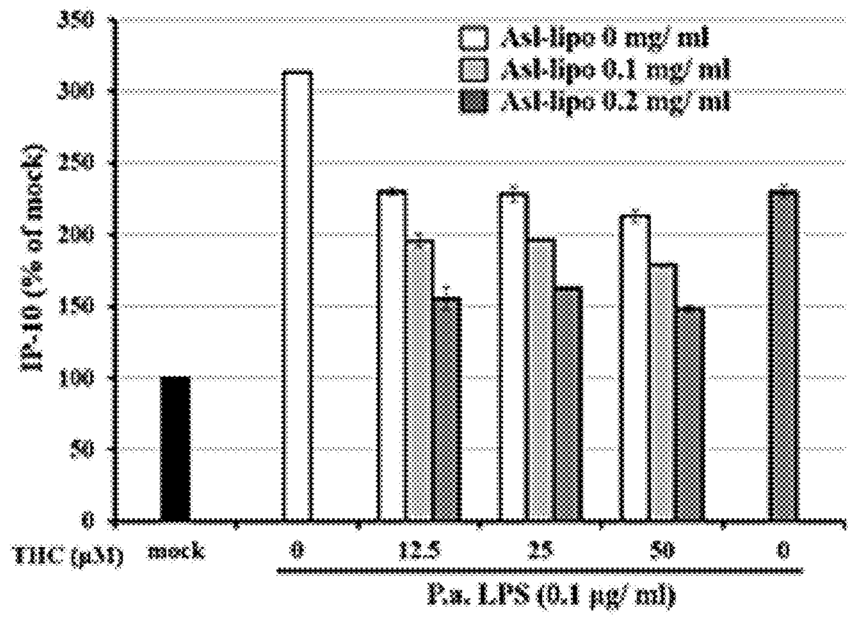
FIG. 7D is a diagram showing the relationship between the concentration of the aquatic liposomes encapsulating tetrahydrocurcumin (THC) and the concentration of the cytokine IP-10 produced by the microglia (BV-2) due to the induction of *P. aeruginosa* according to the embodiment of the present invention.
Figure 7E:
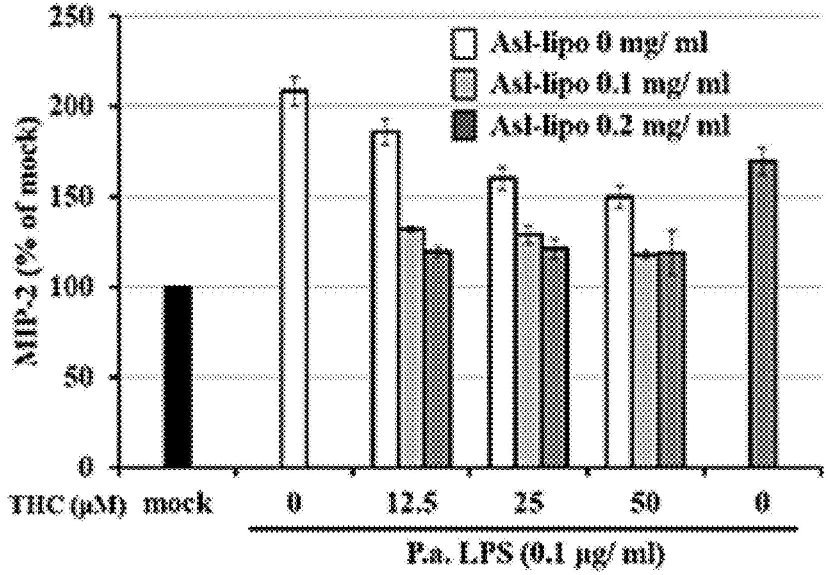
FIG. 7E is a diagram showing the relationship between the concentration of the aquatic liposomes encapsulating tetrahydrocurcumin (THC) and the concentration of the cytokine MIP-2 produced by the microglia (BV-2) due to the induction of *P. aeruginosa* according to the embodiment of the present invention.

The influence of the aquatic liposome (Asl-lipo) encapsulating tetrahydrocurcumin (THC) on the induced inflammatory response of the microglia (BV-2) is determined. The current experiment includes the following steps: the aquatic liposomes (Asl-lipo) with the mixed concentration of 0 mg/ml, 0.1 mg/ml, and 0.2 mg/ml and tetrahydrocurcumin (THC) with the effective amount of 0 μM, 12.5 μM, 25 μM, and 50 μM are provided; each of the aquatic liposomes (Asl-lipo) is mixed with the tetrahydrocurcumin (THC) with different effective amounts and then the ultrasonic oscillation is performed; each of the aquatic liposomes (Asl-lipo) encapsulating tetrahydrocurcumin (THC) is transported into the microglia (BV-2); afterwards, *Pseudomonas aeruginosa* (*P. aeruginosa*) Lipopolysaccharide (LPS) is added for reaction over 24 hours; the levels of inflammatory mediators related to the inflammation is analyzed, wherein the inflammatory mediators include NO (FIG. 7A), TNF-α (FIG. 7B), IL-6 (FIG. 7C), IP-10 (FIG. 7D), and MIP-2 (FIG. 7E); in the mock, phosphate buffered saline is applied; in the control group, the mixed concentration of the aquatic liposome (Asl-lipo) is 0 mg/ml and no tetrahydrocurcumin (THC) is included; in the experimental group, the aquatic liposome (Asl-lipo) (0 mg/ml, 0.1 mg/ml, and 0.2 mg/ml) encapsulating tetrahydrocurcumin (THC) (0 μM, 12.5 μM, 25 μM, and 50 μM) is prepared. The group including the aquatic liposome (Asl-lipo) with the mixed concentration of 0-0.2 mg/ml and tetrahydrocurcumin (THC) with the effective amount of 0-50 μM is to determine the anti-inflammatory effect of the aquatic liposome (Asl-lipo) when only the aquatic liposome (Asl-lipo) is applied.

The result of the experiment is shown in FIG. 7A to FIG. 7E. In the control group, after the microglia (BV-2) is induced by *P. aeruginosa* LPS, the levels of the inflammatory mediators (including inflammatory factor: NO; cytokines: TNF-α, IL-6, IP-10, and MIP-2) are significantly increased compared to the mock. In the experimental group, the levels of the inflammatory mediators (including NO, TNF-α, IL-6, IP-10, and MIP-2) measured from the aquatic liposome (Asl-lipo) (0 mg/ml, 0.1 mg/ml, and 0.2 mg/ml) encapsulating tetrahydrocurcumin (THC) (12.5 μM, 25 μM, and 50 μM) are decreased compared to the control group; when the mixed concentration of the aquatic liposome (Asl-lipo) is 0.1 mg/ml or 0.2 mg/ml and the effective amount of tetrahydrocurcumin (THC) encapsulated is 12.5 μM, 25 μM, or 50 μM, the effect of reducing the levels of the inflammatory mediators (including NO, TNF-α, IL-6, IP-10, and MIP-2) is more significant; when the effective amount of tetrahydrocurcumin (THC) increases (25 μM and 50 μM), the levels of the inflammatory mediators are decreased; the aquatic liposome (Asl-lipo) (0.2 mg/ml) encapsulating tetrahydrocurcumin (THC) (25 μM) and the aquatic liposome (Asl-lipo) (0.2 mg/ml) encapsulating tetrahydrocurcumin (THC) (50 μM) in the experimental group provide a better effect of reducing the levels of the inflammatory mediators, indicating that the aquatic liposome (Asl-lipo) (0.2 mg/ml) encapsulating tetrahydrocurcumin (THC) (50 μM) in the experimental group could in fact provide a better effect of suppressing the inflammatory response compared to the control group and the combination of the aquatic liposome (Asl-lipo) (0 mg/ml) and tetrahydrocurcumin (THC) (12.5 μM, 25 μM, and 50 μM) in the experimental group. In comparison, the combination only including the aquatic liposome (Asl-lipo) (0.2 mg/ml) does not provide a significant effect of reducing the levels of the cytokines. Accordingly, the aquatic liposome (Asl-lipo) encapsulating tetrahydrocurcumin (THC) could enter the microglia (BV-2) to reduce the levels of the inflammatory mediators due to the inflammatory response induced by *P. aeruginosa* LPS, thereby relieving the inflammation of the cells.

Figure 7F:
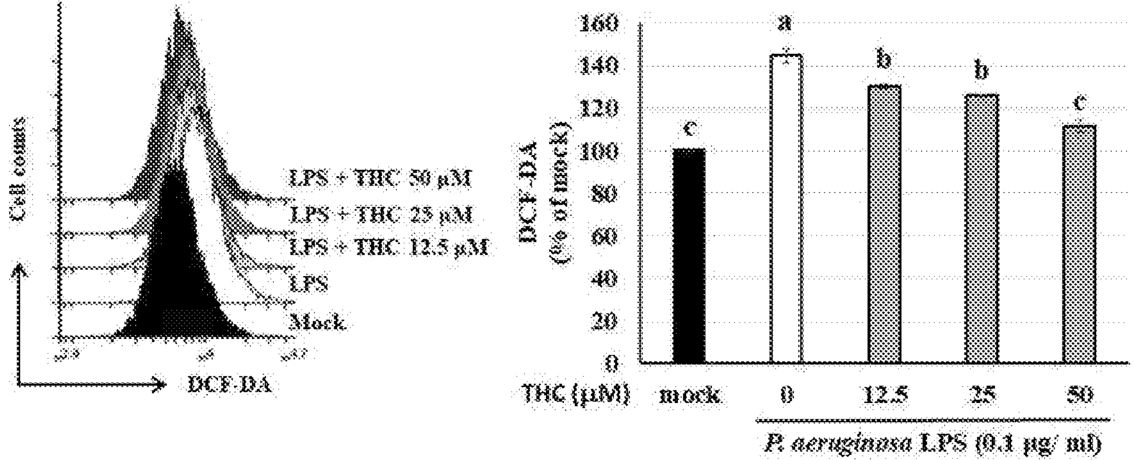
FIG. 7F is a diagram showing the relationship between the concentration of the aquatic liposomes encapsulating tetrahydrocurcumin (THC) and the concentration of the reactive oxygen species (ROS) produced by the microglia (BV-2) due to the induction of *P. aeruginosa* according to the embodiment of the present invention.

Referring to FIG. 7F, the experimental group shows a better effect of suppressing the reactive oxygen species (ROS) production of the microglia (BV-2). In the current experiment, the reactive oxygen species (ROS) is analyzed by DCFH-DA (2',7'-dichlorodihydrofluorescein diacetate), which is a chemical fluorescence substance commonly used in measuring $H_2O_2$. DCFH-DA could freely pass through the cell membrane. After DCFH-DA enters the cell, DCFH-DA is converted by esterase in the cell to DCFH; at that time, DCFH could not freely pass through the cell membrane and is remained within the cell. DCFH is oxidized by $H_2O_2$ in the cell to DCF (dichlorofluorescein) Upon the activation by the wavelength of 450-490 nm, fluorescence at the wavelength of 515-550 nm is emitted. The fluorescence content in the cell is measured by a flow cytometer and therefore the amount of $H_2O_2$ produced in the cell is deduced.

The current experiment makes use of the mock, the control group, and the experimental group processed with the microglia (BV-2) as aforementioned. In the experimental group, the aquatic liposome (Asl-lipo) (0.2 mg/ml) encapsulating tetrahydrocurcumin (THC) (12.5 μM, 25 μM, and 50 μM) is prepared. The mock, the control group, and the experimental group are processed with the growth medium actinodaphnine for 1 hour; afterwards, 10 μM of DCFH-DA is added for reaction over 30 min; rinsing with phosphate buffered saline (PBS) is performed, and then 500 μl of trypsin/0.01% EDTA is added and the Petri dish is left at 37° C. for reaction over 5 min; the cells are detached from the Petri dish; then a culture fluid is added to neutralize trypsin; centrifugation is performed and a supernatant is removed; the reactive oxygen species (ROS) contents of the microglia (BV-2) of the mock, the control group, and the experimental group are measured by the flow cytometer.

The result of the experiment is shown in FIG. 7F. In the experimental group, the aquatic liposome (Asl-lipo) encapsulating tetrahydrocurcumin (THC) could effectively suppress the activity of the reactive oxygen species (ROS), wherein the aquatic liposome (Asl-lipo) (0.2 mg/ml) encapsulating tetrahydrocurcumin (THC) (50 μM) in the experimental group could significantly reduce the level of the reactive oxygen species (ROS).

5. Determination of the Effect of the Aquatic Liposome (Asl-lipo) Encapsulating Tetrahydrocurcumin (THC) on the Reactive Oxygen Species (ROS) Production and Apoptotic Rate of the Retinal Pigment Epithelium Cells (ARPE-19) With Lesion Due to the Induction of Sodium Iodate ($NaIO_3$)

In the current experiment, the mixed concentrations of the aquatic liposomes (Asl-lipo) are 0 mg/ml, 0.1 mg/ml, 0.2 mg/ml, and 0.4 mg/ml, and the effective amounts of tetrahydrocurcumin (THC) are 0 μM, 12.5 μM, 25 μM, and 50 μM. In the mock, phosphate buffered saline (PBS) is used. In the control group, the mixed concentration of the aquatic liposome (Asl-lipo) is 0 mg/ml and no tetrahydrocurcumin (THC) is provided. In the experimental group, the aquatic liposome (Asl-lipo) (0 mg/ml, 0.1 mg/ml, 0.2 mg/ml, and 0.4 mg/ml) encapsulating tetrahydrocurcumin (THC) (0 μM, 12.5 μM, 25 μM, and 50 μM) is prepared, and the ultrasonic oscillation at 40 kHz is performed for 20 min. The combination of the aquatic liposome (Asl-lipo) with the mixed concentration of 0-0.4 mg/ml and tetrahydrocurcumin (THC) with the effective amount of 0-50 μM is to determine the performance of the aquatic liposome (Asl-lipo) when only the aquatic liposome (Asl-lipo) is applied.

The retinal pigment epithelium cells (ARPE-19) are incubated in DMEM (Dulbecco's Modified Eagle Medium) at 37° C. and 5% $CO_2$ until the cells are attached to the Petri dish; The microculture tetrazolium test includes the following steps: the retinal pigment epithelium cells (ARPE-19) are incubated at $2.5\times10^5$ cell/well in a 12-well plate; the mock, the control group, and the experimental group are respectively injected into the 12-well plate containing the retinal pigment epithelium cells (ARPE-19); the 12-well plate is left for reaction over 1.5 hours; afterwards, 6 mM of sodium iodate ($NaIO_3$) is respectively added to the 12-well plate of the experimental group and the 12-well plate of the control group for induction over 24 hours;

after the reaction is completed, a supernatant is removed; 500 μl of DMEM having CCK-8 (10 μl of CCK-8 is added to 500 μl of DMEM) is added; incubation at a 5% $CO_2$ and 7° C. incubator is performed for 4 hours; finally, the absorbance at 570 nm is measured by a spectrophotometer; while the absorbance of the mock measured is quantified to be 100%, the cell viabilities of the retinal pigment epithelium cells (ARPE-19) of the experimental group and the control group are obtained accordingly.

Figure 8A:
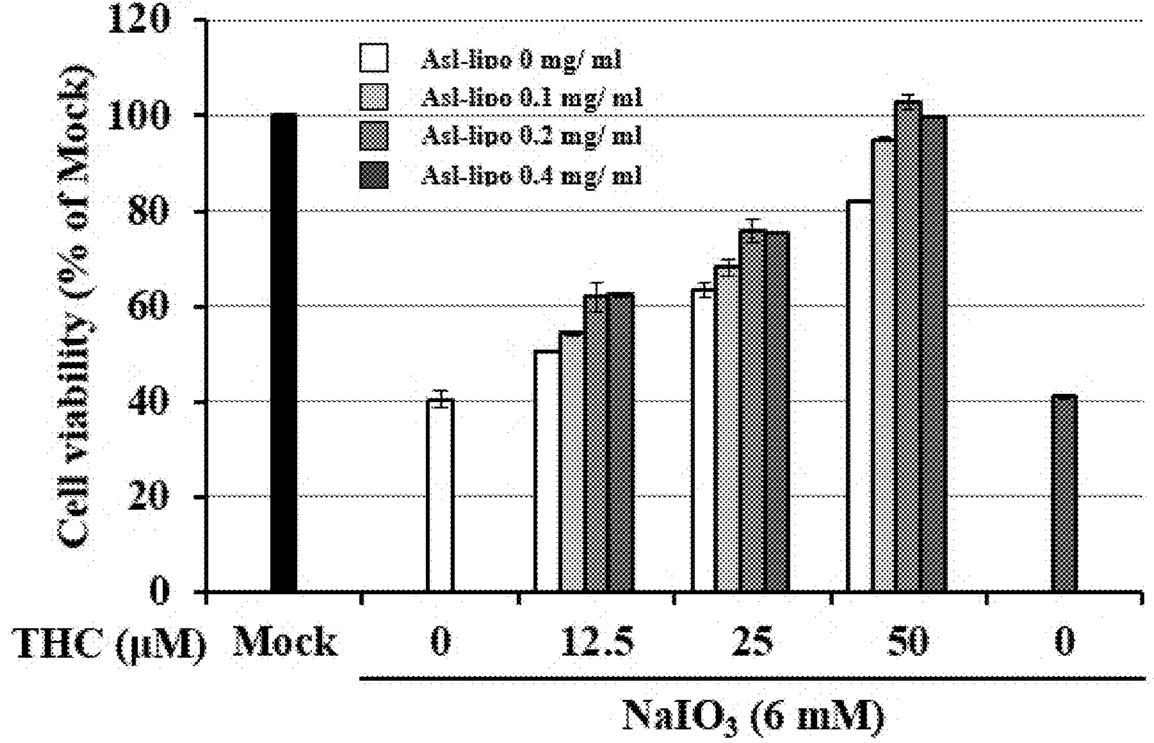
FIG. 8A is a diagram showing the relationship between the concentration of the aquatic liposomes encapsulating tetrahydrocurcumin (THC) and the cell viability of the retinal pigment epithelium cells (ARPE-19) with the lesion due to the induction of sodium iodate according to the embodiment of the present invention.

The result of the experiment is shown in FIG. 8A. In the control group, after the induction sodium iodate ($NaIO_3$), the cell viability of the retinal pigment epithelium cells (ARPE-19) of the control group is lowered to about 40% compared to the mock. In the experimental group, the cell viability of the experimental group that is provided with the aquatic liposome (Asl-lipo) (0 mg/ml, 0.1 mg/ml, 0.2 mg/ml, and 0.4 mg/ml) encapsulating tetrahydrocurcumin (THC) (12.5 μM, 25 μM, and 50 μM) is greater than the cell viability of the control group. Upon the condition that the effective amount of tetrahydrocurcumin (THC) remains unchanged, the cell viability of the retinal pigment epithelium cells (ARPE-19) increases with the increase in the mixed concentration of the aquatic liposome (Asl-lipo). Moreover, upon the condition that the mixed concentration of the aquatic liposome (Asl-lipo) remains unchanged, the cell viability of the retinal pigment epithelium cells (ARPE-19) increases with the increase in the effective amount of tetrahydrocurcumin (THC) effective amount. The aquatic liposome (Asl-lipo) (0 mg/ml, 0.1 mg/ml, 0.2 mg/ml, and 0.4 mg/ml) encapsulating tetrahydrocurcumin (THC) (12.5 μM, 25 μM, and 50 μM) reduces the apoptosis of the retinal pigment epithelium cells (ARPE-19) and could increase the cell viability more effectively than the aquatic liposome (Asl-lipo) that is solely provided.

The reactive oxygen species (ROS) is analyzed by DCFH-DA (2',7'-dichlorodihydrofluorescein diacetate), a chemical fluorescence substance commonly used to measure $H_2O_2$. DCFH-DA could freely pass through the cell membrane. After DCFH-DA enters the cell, DCFH-DA is converted by esterase in the cell to DCFH; at that time, DCFH could not freely pass through the cell membrane and is remained within the cell. DCFH is oxidized by $H_2O_2$ in the cell to DCF (dichlorofluorescein) Upon the activation by the wavelength of 450-490 nm, fluorescence at the wavelength of 515-550 nm is emitted. The amount of $H_2O_2$ produced in the cells can be deduced by measuring the fluorescence content within the cells using flow cytometry.

The current experiment makes use of the mock, the control group, and the experimental group processed with the retinal pigment epithelium cells (ARPE-19) as aforementioned. In the experimental group, the aquatic liposome (Asl-lipo) (0 mg/ml, 0.1 mg/ml, and 0.2 mg/ml) encapsulating tetrahydrocurcumin (THC) (0 μM, 12.5 μM, 25 μM, and 50 μM) is prepared. The combination of the aquatic liposome (Asl-lipo) with the mixed concentration of 0-0.2 mg/ml and tetrahydrocurcumin (THC) with the effective amount of 0-50 μM is to determine the performance of the aquatic liposome (Asl-lipo) when only the aquatic liposome (Asl-lipo) is applied.

Figure 8B:
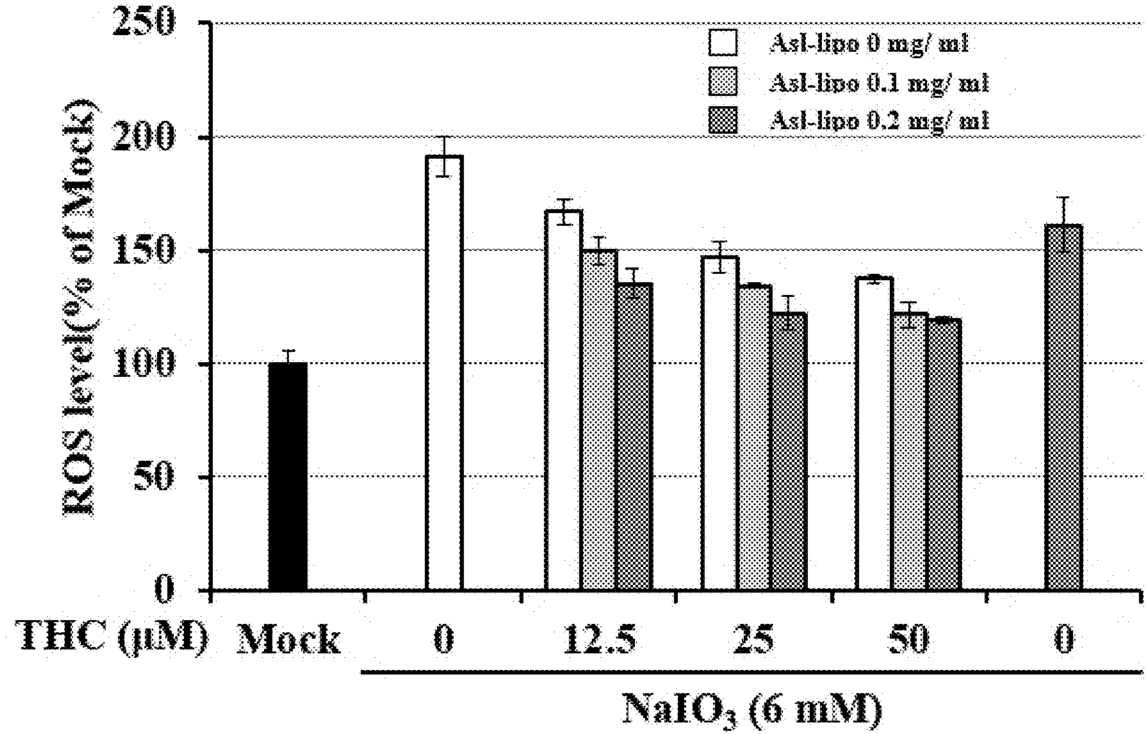
FIG. 8B is a diagram showing the relationship between the concentration of the aquatic liposomes encapsulating tetrahydrocurcumin (THC) and the reactive oxygen species (ROS) level of the retinal pigment epithelium cells (ARPE-19) with the lesion due to the induction of sodium iodate according to the embodiment of the present invention.

The result of the experiment is shown in FIG. 8B. In the control group, after the retinal pigment epithelium cells (ARPE-19) were treated with sodium iodate ($NaIO_3$), the relative performance of the reactive oxygen species (ROS) measured in the control group is above 150%, showing that the reactive oxygen species (ROS) performance level of the retinal pigment epithelium cells (ARPE-19) of the control group after the induction is significantly increased. The reactive oxygen species (ROS) performance level of the experimental group is decreased compared to the control group, wherein upon the condition that the effective amount of tetrahydrocurcumin (THC) remains unchanged, the reactive oxygen species (ROS) performance level of the retinal pigment epithelium cells (ARPE-19) decreases with the increase in the mixed concentration of the aquatic liposome (Asl-lipo); moreover, upon the condition that the mixed concentration of the aquatic liposome (Asl-lipo) remains unchanged, the reactive oxygen species (ROS) performance level of the retinal pigment epithelium cells (ARPE-19) decreases with the increase in the effective amount of tetrahydrocurcumin (THC); the aquatic liposome (Asl-lipo) (0 mg/ml, 0.1 mg/ml, and 0.2 mg/ml) encapsulating tetrahydrocurcumin (THC) (12.5 μM, 25 μM, and 50 μM) provides a better effect of suppressing the reactive oxygen species (ROS) performance level than the aquatic liposome (Asl-lipo) provided solely.

The apoptosis experiment is to observe tetrahydrocurcumin (THC) entering the cells and the apoptosis of the retinal pigment epithelium cells (ARPE-19) by using Annexin V/Propidium iodide (PI). As aforementioned, the apoptosis experiment uses the mock, control, and experimental groups observed by using Annexin V/Propidium iodide (PI). Flow cytometer (FACSCalibur flow cytometer) detects green fluorescence wavelength (Annexin V-FITC) at 490 nm~525 nm and red fluorescence wavelength (PI) at 590 nm. Fluorescence quantitation is performed on the mock, the control group, and the experimental group. In the experimental group, the aquatic liposome (Asl-lipo) (0 mg/ml, 0.1 mg/ml, and 0.2 mg/ml) encapsulating the tetrahydrocurcumin (THC) (0 μM, 12.5 μM, 25 μM, and 50 μM) is prepared. The combination of the aquatic liposome (Asl-lipo) with the mixed concentration of 0-0.2 mg/ml and tetrahydrocurcumin (THC) with the effective amount of 0-50 μM is to examine the performance of the aquatic liposome (Asl-lipo) when only the aquatic liposome (Asl-lipo) is applied.

The cells of the mock, the control group, and the experimental group are classified into four quadrants based on the fluorescence performance of the standard sample: [Q3-1=Annexin V(−), PI(+): Q3-2=Annexin V(+), PI(+); Q3-3=Annexin V(−), PI(−); Q3-4=Annexin V(+), PI(−)]. The apoptotic rate is a relative percentage of late apoptotic cells Q3-2 to early apoptotic cells Q3-4.

Figure 8C:
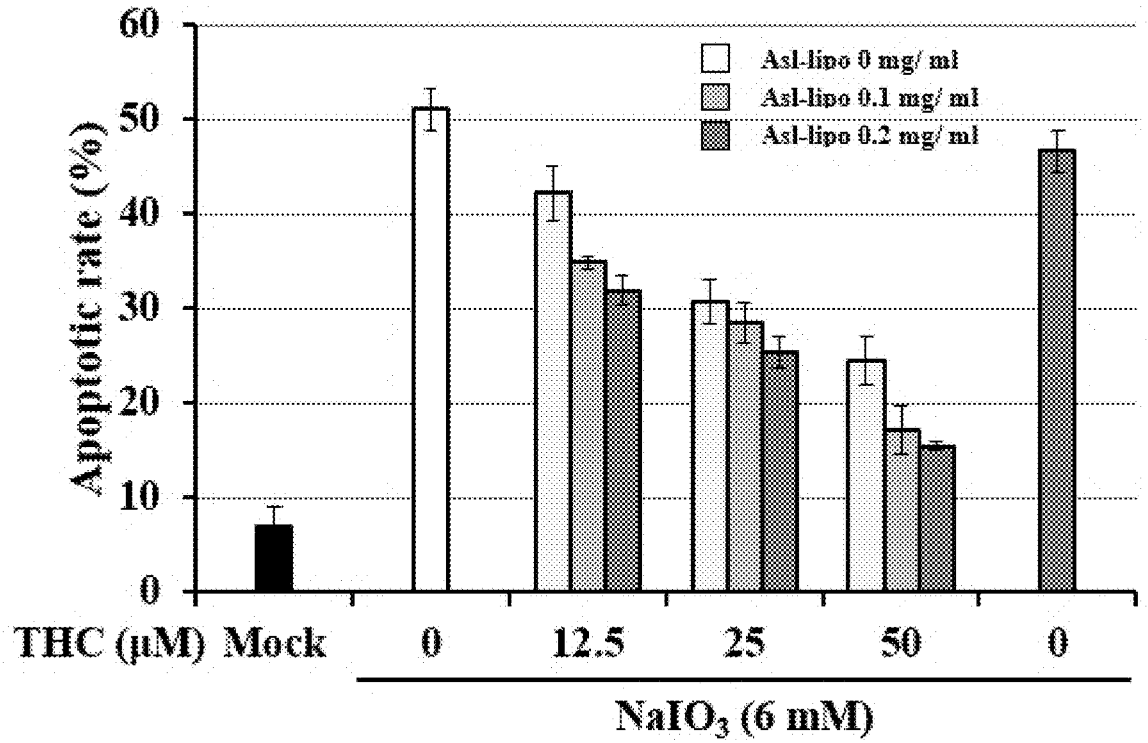
FIG. 8C is a diagram showing the relationship between the concentration of the aquatic liposomes encapsulating tetrahydrocurcumin (THC) and the apoptotic rate of the retinal pigment epithelium cells (ARPE-19) with the lesion due to the induction of sodium iodate according to the embodiment of the present invention

The result of the experiment is shown in FIG. 8C. In the control group, after the induction of sodium iodate (NaIO3) in the retinal pigment epithelium cells (ARPE-19), the apoptotic rate of the control group is above 50%. The apoptotic rate of the experimental group is decreased relative to the control group. Upon the condition that the effective amount of tetrahydrocurcumin (THC) remains unchanged, the apoptotic rate of the retinal pigment epithelium cells (ARPE-19) decreases with the increase in the mixed concentration of the aquatic liposome (Asl-lipo). Moreover, upon the condition that the mixed concentration of the aquatic liposome (Asl-lipo) remains unchanged, the apoptotic rate of the retinal pigment epithelium cells (ARPE-19) decreases with the increase in the effective amount of tetrahydrocurcumin (THC). The aquatic liposome (Asl-lipo) (0 mg/ml, 0.1 mg/ml, and 0.2 mg/ml) encapsulating tetrahydrocurcumin (THC) (12.5 μM, 25 μM, and 50 μM) provides a better effect of reducing the level of the reactive oxygen species (ROS), which is induced by sodium iodate ($NaIO_3$), than the aquatic liposome (Asl-lipo) that is solely applied, showing that the aquatic liposome (Asl-lipo) encapsulating tetrahydrocurcumin (THC) could inhibit apoptosis and increase cell viability.

It must be pointed out that the embodiments described above are only some preferred embodiments of the present invention. All equivalent structures which employ the concepts disclosed in this specification and the appended claims should fall within the scope of the present invention.

What is claimed is:

1. An aquatic liposome encapsulating a natural compound, wherein an average particle size (a median particle size) of the aquatic liposome encapsulating the natural compound ranges from 80 nm to 200 nm, and the aquatic liposome is obtained by extracting from *Acipenser sinensis*.

2. The aquatic liposome encapsulating the natural compound as claimed in claim 1, wherein the natural compound comprises tetrahydrocurcumin (THC) or quercetin, and an effective amount of the natural compound encapsulated in the aquatic liposome ranges from 10 μM to 60 μM.

3. The aquatic liposome encapsulating the natural compound as claimed in claim 1, wherein a mixed concentration of the aquatic liposome ranges from 0.05 mg/ml to 1.0 mg/ml; the aquatic liposome and the natural compound are mixed and an ultrasonic oscillation is performed, wherein a frequency of the ultrasonic oscillation ranges from 30 kHz to 50 kHz and a oscillation time ranges from 5 min to 60 min, so that the natural compound is encapsulated in the aquatic liposome; the average particle size (the median particle size) of the aquatic liposome encapsulating the natural compound ranges from 100 nm to 150 nm.

4. The aquatic liposome encapsulating the natural compound as claimed in claim 2, wherein a mixed concentration of the aquatic liposome ranges from 0.05 mg/ml to 1.0 mg/ml; the aquatic liposome and the natural compound are mixed and an ultrasonic oscillation is performed, wherein a frequency of the ultrasonic oscillation ranges from 30 kHz to 50 kHz and an oscillation time ranges from 5 min to 60 min, so that the natural compound is encapsulated in the aquatic liposome; the average particle size (the median particle size) of the aquatic liposome encapsulating the natural compound ranges from 100 nm to 150 nm.

5. The aquatic liposome encapsulating the natural compound as claimed in claim 3, wherein the mixed concentration of the aquatic liposome ranges from 0.1 mg/ml to 0.5 mg/ml; after the aquatic liposome and the natural compound are mixed and the ultrasonic oscillation is performed, an encapsulation efficiency of the aquatic liposome is greater than or equal to 50%, and an effective amount of the natural compound encapsulated in the aquatic liposome ranges from 12.5 μM to 50 μM.

6. The aquatic liposome encapsulating the natural compound as claimed in claim 4, wherein the mixed concentration of the aquatic liposome ranges from 0.1 mg/ml to 0.5 mg/ml; after the aquatic liposome and the natural compound are mixed and the ultrasonic oscillation is performed, an encapsulation efficiency of the aquatic liposome is greater than or equal to 50%, and the effective amount of the natural compound encapsulated in the aquatic liposome ranges from 12.5 μM to 50 μM.

7. The aquatic liposome encapsulating the natural compound as claimed in claim 5, wherein the mixed concentration of the aquatic liposome ranges from 0.2 mg/ml to 0.4 mg/ml; after the aquatic liposome and the natural compound are mixed and the ultrasonic oscillation is performed, the encapsulation efficiency of the aquatic liposome is greater than or equal to 65%, and the effective amount of the natural compound encapsulated in the aquatic liposome ranges from 25 μM to 50 μM.

8. The aquatic liposome encapsulating the natural compound as claimed in claim 6, wherein the mixed concentration of the aquatic liposome ranges from 0.2 mg/ml to 0.4 mg/ml; after the aquatic liposome and the natural compound are mixed and the ultrasonic oscillation is performed, the encapsulation efficiency of the aquatic liposome is greater than or equal to 65%, and the effective amount of the natural compound encapsulated in the aquatic liposome ranges from 25 μM to 50 μM.

9. The aquatic liposome encapsulating the natural compound as claimed in claim 2, wherein the aquatic liposome encapsulating the natural compound is capable of entering microglia and reducing inflammatory mediator levels of an inflammatory response induced by *Pseudomonas aeruginosa.*

10. The aquatic liposome encapsulating the natural compound as claimed in claim 3, wherein the aquatic liposome encapsulating the natural compound is capable of entering retinal pigment epithelium cells and inhibiting a reactive oxygen species level induced by sodium iodate.

11. The aquatic liposome encapsulating the natural compound as claimed in claim 4, wherein the aquatic liposome encapsulating the natural compound is capable of entering retinal pigment epithelium cells and inhibiting a reactive oxygen species level induced by sodium iodate.

12. A manufacturing method of an aquatic liposome encapsulating a natural compound, comprising:

step S1: providing an aquatic liposome and mixing the aquatic liposome with the natural compound, wherein a mixed concentration of the aquatic liposome ranges from 0.05 mg/ml to 1.0 mg/ml, the aquatic liposome is obtained by extracting from *Acipenser sinensis*, and the mixed concentration of the aquatic liposome ranges from 0.1 mg/ml to 0.5 mg/ml;

step S2: performing an ultrasonic oscillation after mixing the aquatic liposome and the natural compound, so that the natural compound is encapsulated in the aquatic liposome; and step S3: measuring the aquatic liposome, wherein an average particle size (a median particle size) of the aquatic liposome encapsulating the natural compound ranges from 80 nm to 200 nm.

13. The manufacturing method as claimed in claim 12, wherein the natural compound comprises tetrahydrocurcumin (THC) or quercetin; and an effective amount of the natural compound encapsulated in the aquatic liposome ranges from 10 μM to 60 μM.

14. The manufacturing method as claimed in claim 13, wherein in step S2, a frequency of the ultrasonic oscillation ranges from 30 kHz to 50 kHz and an oscillation time ranges from 5 min to 60 min.

15. The manufacturing method as claimed in claim 14, wherein in step S3, the average particle size (the median particle size) of the aquatic liposome encapsulating the natural compound ranges from 100 nm to 150 nm; when the mixed concentration of the aquatic liposome ranges from 0.1 mg/ml to 0.5 mg/ml, an encapsulation efficiency of the aquatic liposome after mixing the aquatic liposome and the natural compound and performing the ultrasonic oscillation is greater than or equal to 50%, and the effective amount of the natural compound encapsulated in the aquatic liposome ranges from 12.5 μM to 50 μM.

16. The manufacturing method as claimed in claim 15, wherein in step S1, the mixed concentration of the aquatic liposome ranges from 0.2 mg/ml to 0.4 mg/ml; in step S3, when the mixed concentration of the aquatic liposome ranges from 0.2 mg/ml to 0.4 mg/ml, the encapsulation efficiency of the aquatic liposome after mixing the aquatic liposome and the natural compound and performing the ultrasonic oscillation is greater than or equal to 65%, and the effective amount of the natural compound encapsulated in the aquatic liposome ranges from 25 μM to 50 μM.

* * * * *